(12) United States Patent
Chapman

(10) Patent No.: US 8,673,876 B2
(45) Date of Patent: Mar. 18, 2014

(54) PHARMACEUTICAL COMBINATIONS FOR TREATMENT OF SPECIFIC CANCERS

(75) Inventor: Mark Chapman, San Diego, CA (US)

(73) Assignee: Ardea Biosciences Inc., San Diego, CA (US)

(\*) Notice: Subject to any disclaimer, the term of this patent is extended or adjusted under 35 U.S.C. 154(b) by 83 days.

(21) Appl. No.: 13/255,278

(22) PCT Filed: Mar. 11, 2010

(86) PCT No.: PCT/US2010/027060
§ 371 (c)(1),
(2), (4) Date: Nov. 17, 2011

(87) PCT Pub. No.: WO2010/105110
PCT Pub. Date: Sep. 16, 2010

(65) Prior Publication Data
US 2012/0071435 A1    Mar. 22, 2012

Related U.S. Application Data

(60) Provisional application No. 61/159,403, filed on Mar. 11, 2009.

(51) Int. Cl.
*A01N 43/04* (2006.01)
*A61K 31/70* (2006.01)
*A61K 31/18* (2006.01)

(52) U.S. Cl.
USPC .......................................................... 514/49

(58) Field of Classification Search
None
See application file for complete search history.

(56) References Cited

U.S. PATENT DOCUMENTS 6,822,001 B2 * 11/2004 Schwendner et al. ........ 514/601
7,417,055 B2    8/2008 Cannizzaro et al.
2008/0058340 A1 * 3/2008 Maderna et al. ........ 514/252.12
2009/0017050 A1    1/2009 Powell et al.
2009/0047365 A1 * 2/2009 Owa et al. .................... 424/649

FOREIGN PATENT DOCUMENTS

| DE | 10 2008 031039 | 12/2009 |
|---|---|---|
| WO | WO-01 32155 | 5/2001 |
| WO | WO-03 030908 | 4/2003 |
| WO | WO-2006 066267 | 6/2003 |
| WO | WO-2006 076463 | 7/2006 |
| WO | WO 2007014011 A2 * | 2/2007 |
| WO | WO-2009 018233 | 2/2009 |

OTHER PUBLICATIONS

Doemling Alexander, "Use of N-phenylquinazolin-4-amine derivatives as receptor tyrosine kinase inhibitors for accompanying treatment of organ transplantations," Espacenet, Publication Date: Dec. 31, 2009; English Abstract of DE-10 2008 031039.
International Search Report for PCT/US2010/027060 dated Aug. 18, 2010.
Iverson, C. et al., "RDEA119/BAY 869766: A potent, selective, allosteric inhibitor of MEK½ for the treatment of cancer," Cancer Research, 2009, vol. 69, No. 17, pp. 6839-6847.

\* cited by examiner

*Primary Examiner* — Layla Bland
(74) *Attorney, Agent, or Firm* — Millen, White, Zelano & Branigan, P.C.

(57) ABSTRACT

The present invention relates to the field of oncology and provides compositions and methods for treating specific cancers, including non small cell lung cancer, breast cancer, thyroid cancer, pancreatic cancer, colon cancer, melanoma, hepatoma and adenocarcinoma. Particularly, compositions and methods involving administration, either simultaneously or sequentially, of pharmaceutical combinations comprising (S)—N-(3,4-difluoro-2-(2-fluoro-4-iodophenylamino)-6-methoxyphenyl)-1-(2,3-dihydroxypropyl)cyclopropane-1-sulfonamide with other compounds, to patients suffering from cancer are described.

17 Claims, 17 Drawing Sheets

Isobologram

Isobolograms for TA1 with TA2 in A549 NSCLC Cells

Isobolograms for TA1 with TA3 in A549 NSCLC Cells

Isobolograms for TA1 with TA3 in MDA-MB231 Breast Cancer Cells

Isobolograms for TA1 with TA3 in SW579 Thyroid Cancer Cells

Isobolograms for TA1 with TA4 in NSCLC Cells

Isobolograms for TA1 with TA4 in G361 Melanoma Cells

Isobolograms for TA1 with TA4 in MCF-7 Human Breast Cancer Cells

Isobolograms for TA1 with TA4 in MiaPaCa-2 Pancreatic Cells

Isobolograms for TA1 with TA4 in SW579 Thyroid Cancer Cells

Isobolograms for TA1 with TA5 in SW579 Thyroid Cancer Cells

Isobolograms for TA1 with TA6 in G361 Melanoma Cells

Isobolograms for TA1 with TA7 in MCF-7 Breast Cancer Cells

Isobolograms for TA1 with TA7 in SW579 ThyroidCancer Cells

TA1 with TA8 in Human adenocarcinoma AGS cells treated for 3 days (two different doses)

TA1 with TA8 in Hepatoma Hep3B cells treated for 4 days

TA1 with TA9 in HCT-116 Colon Cancer cells

PHARMACEUTICAL COMBINATIONS FOR TREATMENT OF SPECIFIC CANCERS

This application claims the benefit of the filing date of U.S. Provisional Application Ser. No. 61/159,403 filed Mar. 11, 2009, which is incorporated by reference herein.

BACKGROUND OF THE INVENTION

Neoplasias are benign or malignant. Cancers are a group of maligantant neoplasias. Cancers are characterized by the presence of cells that display uncontrolled growth, invasion, and sometimes metastasis. Benign neoplasias, which are self-limited, do not invade or metastasize.

Oncogenes are mutated forms of certain normal cellular genes ("proto-oncogenes"). In certain instances, oncogenes encode abnormal versions of signal pathway components, (e.g., receptor tyrosine kinases, serine-threonine kinases, or downstream signaling molecules.

SUMMARY OF THE INVENTION

Disclosed herein, in certain embodiments, is a method of treating non-small cell lung cancer comprising administering to an individual in need thereof a synergistic combination of: a therapeutically-effective amount of (S)—N-(3,4-difluoro-2-(2-fluoro-4-iodophenylamino)-6-methoxyphenyl)-1-(2,3-dihydroxypropyl)cyclopropane-1-sulfonamide, a salt thereof, or a polymorph thereof; and an effective amount of 3-(6,7-bis(2-methoxyethoxy)quinazolin-4-ylamino)benzonitrile:

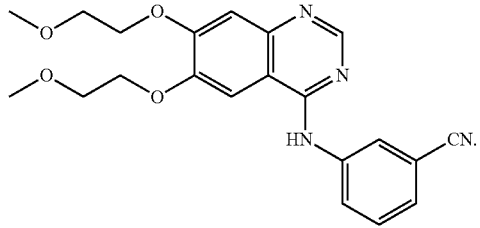 [SMILES: COCCOc1cc2ncnc(Nc3cccc(C#N)c3)c2cc1OCCOC]

Disclosed herein, in certain instances, is A composition comprising: a therapeutically-effective amount of (S)—N-(3,4-difluoro-2-(2-fluoro-4-iodophenylamino)-6-methoxyphenyl)-1-(2,3-dihydroxypropyl)cyclopropane-1-sulfonamide, a salt thereof, or a polymorph thereof; and 3-(6,7-bis(2-methoxyethoxy)quinazolin-4-ylamino)benzonitrile:

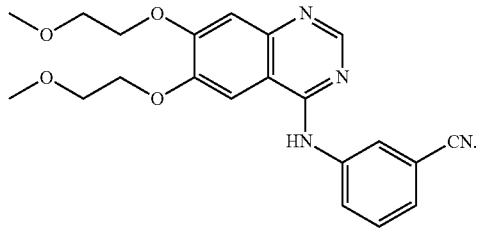 [SMILES: COCCOc1cc2ncnc(Nc3cccc(C#N)c3)c2cc1OCCOC]

Disclosed herein, in certain instances, is a method of treating non-small cell lung cancer, comprising administering to an individual in need thereof a synergistic combination of: a therapeutically-effective amount of (S)—N-(3,4-difluoro-2-(2-fluoro-4-iodophenylamino)-6-methoxyphenyl)-1-(2,3-dihydroxypropyl)cyclopropane-1-sulfonamide, a salt thereof, or a polymorph thereof; and an effective amount of N-(3-chloro-4-fluorophenyl)-7-methoxy-6-(3-morpholinopropoxy)quinazolin-4-amine:

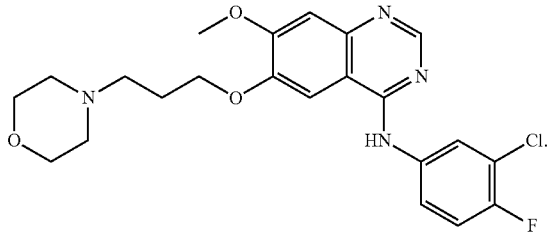 [SMILES: COc1cc2ncnc(Nc3ccc(F)c(Cl)c3)c2cc1OCCCN1CCOCC1]

Disclosed herein, in certain instances, is a method of treating breast cancer, comprising administering to an individual in need thereof a synergistic combination of: a therapeutically-effective amount of (S)—N-(3,4-difluoro-2-(2-fluoro-4-iodophenylamino)-6-methoxyphenyl)-1-(2,3-dihydroxypropyl)cyclopropane-1-sulfonamide, a salt thereof, or a polymorph thereof; and an effective amount of N-(3-chloro-4-fluorophenyl)-7-methoxy-6-(3-morpholinopropoxy)quinazolin-4-amine:

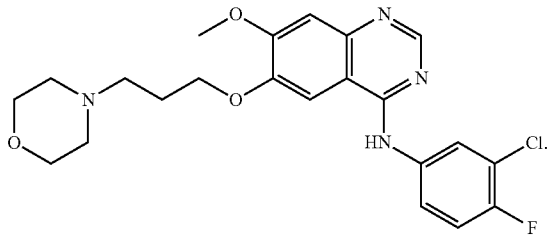 [SMILES: COc1cc2ncnc(Nc3ccc(F)c(Cl)c3)c2cc1OCCCN1CCOCC1]

Disclosed herein, in certain instances, is a method of treating thyroid cancer, comprising administering to an individual in need thereof a synergistic combination of: a therapeutically-effective amount of (S)—N-(3,4-difluoro-2-(2-fluoro-4-iodophenylamino)-6-methoxyphenyl)-1-(2,3-dihydroxypropyl)cyclopropane-1-sulfonamide, a salt thereof, or a polymorph thereof; and an effective amount of N-(3-chloro-4-fluorophenyl)-7-methoxy-6-(3-morpholinopropoxy)quinazolin-4-amine:

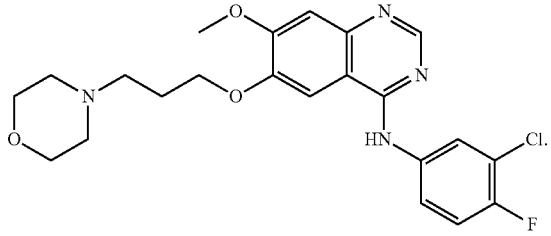 [SMILES: COc1cc2ncnc(Nc3ccc(F)c(Cl)c3)c2cc1OCCCN1CCOCC1]

Disclosed herein, in certain instances, is A composition comprising: (a therapeutically-effective amount of (S)—N-(3,4-difluoro-2-(2-fluoro-4-iodophenylamino)-6-methoxyphenyl)-1-(2,3-dihydroxypropyl)cyclopropane-1-sulfonamide, a salt thereof, or a polymorph thereof; and N-(3-chloro-4-fluorophenyl)-7-methoxy-6-(3-morpholinopropoxy)quinazolin-4-amine:

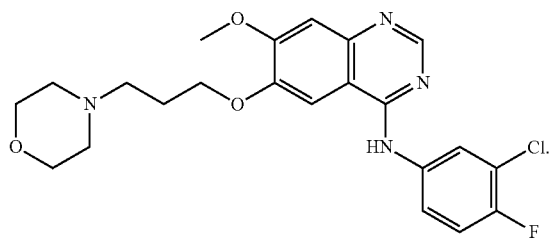 [SMILES: COc1cc2ncnc(Nc3ccc(F)c(Cl)c3)c2cc1OCCCN1CCOCC1]

Disclosed herein, in certain instances, is a method of treating non-small cell lung cancer, comprising administering to an individual in need thereof a synergistic combination of: a therapeutically-effective amount of (S)—N-(3,4-difluoro-2-(2-fluoro-4-iodophenylamino)-6-methoxyphenyl)-1-(2,3-dihydroxypropyl)cyclopropane-1-sulfonamide, a salt thereof, or a polymorph thereof; and an effective amount of 4-amino-1-[3,3-difluoro-4-hydroxy-5-(hydroxymethyl)tetrahydrofuran-2-yl]-1H-pyrimidin-2-one:

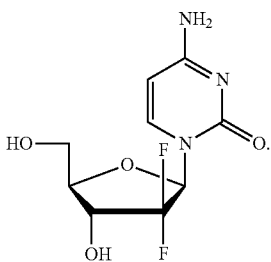 [SMILES: Nc1ccn([C@@H]2O[C@H](CO)[C@H](O)C2(F)F)c(=O)n1]

Disclosed herein, in certain instances, is a method of treating melanoma, comprising administering to an individual in need thereof a synergistic combination of: a therapeutically-effective amount of (S)—N-(3,4-difluoro-2-(2-fluoro-4-iodophenylamino)-6-methoxyphenyl)-1-(2,3-dihydroxypropyl)cyclopropane-1-sulfonamide, a salt thereof, or a polymorph thereof; and an effective amount of 4-amino-1-[3,3-difluoro-4-hydroxy-5-(hydroxymethyl)tetrahydrofuran-2-yl]-1H-pyrimidin-2-one:

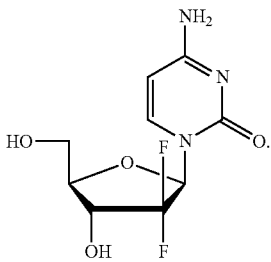 [SMILES: Nc1ccn([C@@H]2O[C@H](CO)[C@H](O)C2(F)F)c(=O)n1]

Disclosed herein, in certain instances, is a method of treating breast cancer, comprising administering to an individual in need thereof a synergistic combination of: a therapeutically-effective amount of (S)—N-(3,4-difluoro-2-(2-fluoro-4-iodophenylamino)-6-methoxyphenyl)-1-(2,3-dihydroxypropyl)cyclopropane-1-sulfonamide, a salt thereof, or a polymorph thereof; and an effective amount of 4-amino-1-[3,3-difluoro-4-hydroxy-5-(hydroxymethyl)tetrahydrofuran-2-yl]-1H-pyrimidin-2-one:

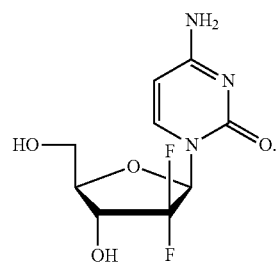 [SMILES: Nc1ccn([C@@H]2O[C@H](CO)[C@H](O)C2(F)F)c(=O)n1]

Disclosed herein, in certain instances, is a method of treating pancreatic cancer, comprising administering to an individual in need thereof a synergistic combination of: a therapeutically-effective amount of (S)—N-(3,4-difluoro-2-(2-fluoro-4-iodophenylamino)-6-methoxyphenyl)-1-(2,3-dihydroxypropyl)cyclopropane-1-sulfonamide, a salt thereof, or a polymorph thereof; and an effective amount of 4-amino-1-[3,3-difluoro-4-hydroxy-5-(hydroxymethyl)tetrahydrofuran-2-yl]-1H-pyrimidin-2-one:

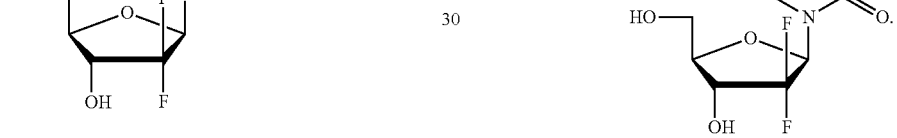

Disclosed herein, in certain instances, is a method of treating thyroid cancer, comprising administering to an individual in need thereof a synergistic combination of: a therapeutically-effective amount of (S)—N-(3,4-difluoro-2-(2-fluoro-4-iodophenylamino)-6-methoxyphenyl)-1-(2,3-dihydroxypropyl)cyclopropane-1-sulfonamide, a salt thereof, or a polymorph thereof; and an effective amount of 4-amino-1-[3,3-difluoro-4-hydroxy-5-(hydroxymethyl)tetrahydrofuran-2-yl]-1H-pyrimidin-2-one:

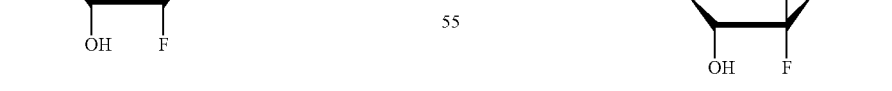

Disclosed herein, in certain instances, is A composition comprising: a therapeutically-effective amount of (S)—N-(3,4-difluoro-2-(2-fluoro-4-iodophenylamino)-6-methoxyphenyl)-1-(2,3-dihydroxypropyl)cyclopropane-1-sulfonamide, a salt thereof, or a polymorph thereof; and 4-amino-1-[3,3-difluoro-4-hydroxy-5-(hydroxymethyl)tetrahydrofuran-2-yl]-1H-pyrimidin-2-one:

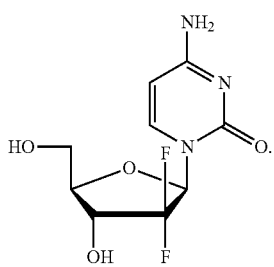 [SMILES: Nc1ccn([C@@H]2O[C@H](CO)[C@H](O)C2(F)F)c(=O)n1]

Disclosed herein, in certain instances, is a method of treating thyroid cancer, comprising administering to an individual in need thereof a synergistic combination of: a therapeutically-effective amount of (S)—N-(3,4-difluoro-2-(2-fluoro-4-iodophenylamino)-6-methoxyphenyl)-1-(2,3-dihydroxypropyl)cyclopropane-1-sulfonamide, a salt thereof, or a polymorph thereof; and an effective amount of N-hydroxy-N'-phenyl-octanediamide:

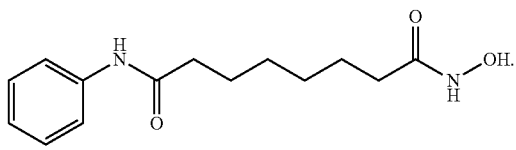 [SMILES: O=C(CCCCCCC(=O)Nc1ccccc1)NO]

Disclosed herein, in certain instances, is A composition comprising: a therapeutically-effective amount of (S)—N-(3,4-difluoro-2-(2-fluoro-4-iodophenylamino)-6-methoxyphenyl)-1-(2,3-dihydroxypropyl)cyclopropane-1-sulfonamide, a salt thereof, or a polymorph thereof; and N-hydroxy-N'-phenyl-octanediamide:

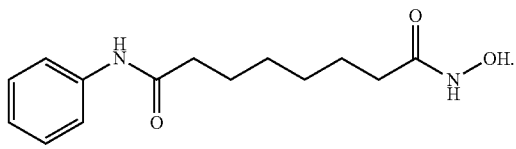 [SMILES: O=C(CCCCCCC(=O)Nc1ccccc1)NO]

Disclosed herein, in certain instances, is a method of treating melanoma, comprising administering to an individual in need thereof a synergistic combination of: a therapeutically-effective amount of (S)—N-(3,4-difluoro-2-(2-fluoro-4-iodophenylamino)-6-methoxyphenyl)-1-(2,3-dihydroxypropyl)cyclopropane-1-sulfonamide, a salt thereof, or a polymorph thereof; and an effective amount of 4-methyl-5-oxo-2,3,4,6,8-pentazabicyclo[4.3.0]nona-2,7,9-triene-9-carboxamide:

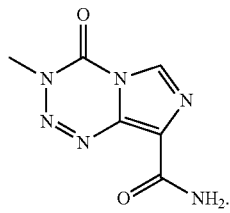

Disclosed herein, in certain instances, is A composition comprising: a therapeutically-effective amount of (S)—N-(3,4-difluoro-2-(2-fluoro-4-iodophenylamino)-6-methoxyphenyl)-1-(2,3-dihydroxypropyl)cyclopropane-1-sulfonamide, a salt thereof, or a polymorph thereof; and 4-methyl-5-oxo-2,3,4,6,8-pentazabicyclo[4.3.0]nona-2,7,9-triene-9-carboxamide:

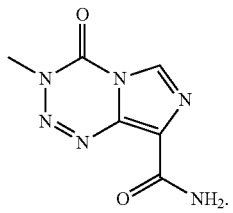

Disclosed herein, in certain instances, is a method of treating breast cancer, comprising administering to an individual in need thereof a synergistic combination of: a therapeutically-effective amount of (S)—N-(3,4-difluoro-2-(2-fluoro-4-iodophenylamino)-6-methoxyphenyl)-1-(2,3-dihydroxypropyl)cyclopropane-1-sulfonamide, a salt thereof, or a polymorph thereof; and an effective amount of N-[3-chloro-4-[(3-fluorophenyl)methoxy]phenyl]-6-[5-[(2-methylsulfonylethylamino)methyl]-2-furyl]quinazolin-4-amine:

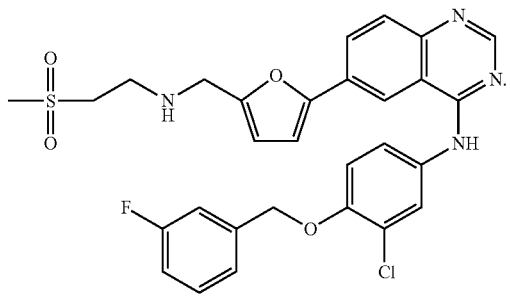 [SMILES: CS(=O)(=O)CCNCc1ccc(-c2ccc3ncnc(Nc4ccc(OCc5cccc(F)c5)c(Cl)c4)c3c2)o1]

Disclosed herein, in certain instances, is a method of treating thyroid cancer, comprising administering to an individual in need thereof a synergistic combination of: a therapeutically-effective amount of (S)—N-(3,4-difluoro-2-(2-fluoro-4-iodophenylamino)-6-methoxyphenyl)-1-(2,3-dihydroxypropyl)cyclopropane-1-sulfonamide, a salt thereof, or a polymorph thereof; and an effective amount of N-[3-chloro-4-[(3-fluorophenyl)methoxy]phenyl]-6-[5-[(2-methylsulfonylethylamino)methyl]-2-furyl]quinazolin-4-amine:

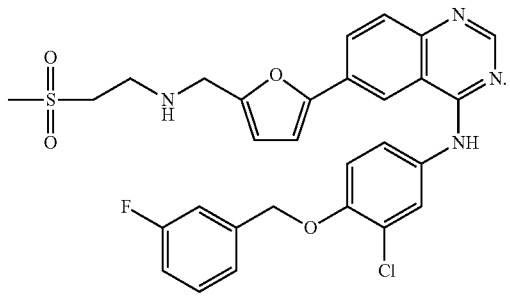 [SMILES: CS(=O)(=O)CCNCc1ccc(-c2ccc3ncnc(Nc4ccc(OCc5cccc(F)c5)c(Cl)c4)c3c2)o1]

Disclosed herein, in certain instances, is A composition comprising: a therapeutically-effective amount of (S)—N-(3,4-difluoro-2-(2-fluoro-4-iodophenylamino)-6-methoxyphenyl)-1-(2,3-dihydroxypropyl)cyclopropane-1-sulfonamide, a salt thereof, or a polymorph thereof; and N-[3-chloro-4-[(3- fluorophenyl)methoxy]phenyl]-6-[5-[(2-methylsulfonyl-ethylamino)methyl]-2-furyl]quinazolin-4-amine:

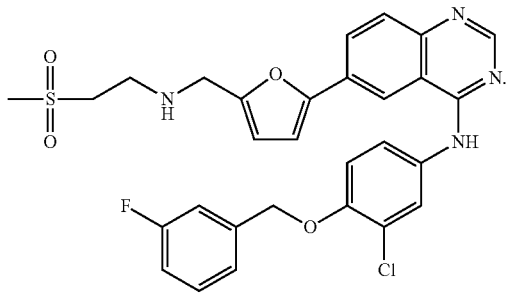 [SMILES: CS(=O)(=O)CCNCc1ccc(-c2ccc3ncnc(Nc4ccc(OCc5cccc(F)c5)c(Cl)c4)c3c2)o1]

Disclosed herein, in certain instances, is a method of treating adenocarcinoma, comprising administering to an individual in need thereof a synergistic combination of: a therapeutically-effective amount of (S)—N-(3,4-difluoro-2-(2-fluoro-4-iodophenylamino)-6-methoxyphenyl)-1-(2,3-dihydroxypropyl)cyclopropane-1-sulfonamide, a salt thereof, or a polymorph thereof; and an effective amount of (1R,2R,4S)-4-{(2R)-2-[(3S,6R,7E,9R,10R,12R,14S,15E,17E,19E, 21S,23S,26R,27R,34aS)-9,27-dihydroxy-10,21-dimethoxy-6,8,12,14,20,26-hexamethyl-1,5,11,28,29-pentaoxo-1,4,5,6,9,10,11,12,13,14,21,22,23,24,25,26,27,28,29,31,32,33,34,34a-tetracosahydro-3H-23,27-epoxypyrido[2,1-c][1,4]oxazacyclohentriacontin-3-yl]propyl}-2-methoxycyclohexyl 3-hydroxy-2-(hydroxymethyl)-2-methylpropanoate:

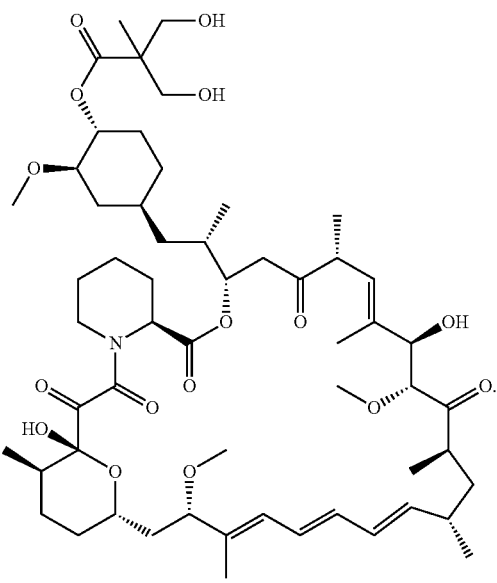 [SMILES: CO[C@H]1C[C@@H]2CC[C@@H](C)[C@@](O)(O2)C(=O)C(=O)N2CCCC[C@H]2C(=O)O[C@H]([C@@H](C)C[C@@H]2CC[C@@H](OC(=O)C(C)(CO)CO)[C@H](OC)C2)CC(=O)[C@H](C)/C=C(\C)[C@@H](O)[C@@H](OC)C(=O)[C@H](C)C[C@H](C)/C=C/C=C/C=C/1C]

Disclosed herein, in certain instances, is a method of treating hepatoma, comprising administering to an individual in need thereof a synergistic combination of: a therapeutically-effective amount of (S)—N-(3,4-difluoro-2-(2-fluoro-4-iodophenylamino)-6-methoxyphenyl)-1-(2,3-dihydroxypropyl)cyclopropane-1-sulfonamide, a salt thereof, or a polymorph thereof; and an effective amount of (1R,2R,4S)-4-{(2R)-2-[(3S,6R,7E,9R,10R,12R,14S,15E,17E,19E,21S,23S,26R,27R,34aS)-9,27-dihydroxy-10,21-dimethoxy-6,8,12,14,20,26-hexamethyl-1,5,11,28,29-pentaoxo-1,4,5,6,9,10,11,12,13,14,21,22,23,24,25,26,27,28,29,31,32,33,34,34a-tetracosahydro-3H-23,27-epoxypyrido[2,1-c][1,4]oxazacyclohentriacontin-3-yl]propyl}-2-methoxycyclohexyl 3-hydroxy-2-(hydroxymethyl)-2-methylpropanoate:

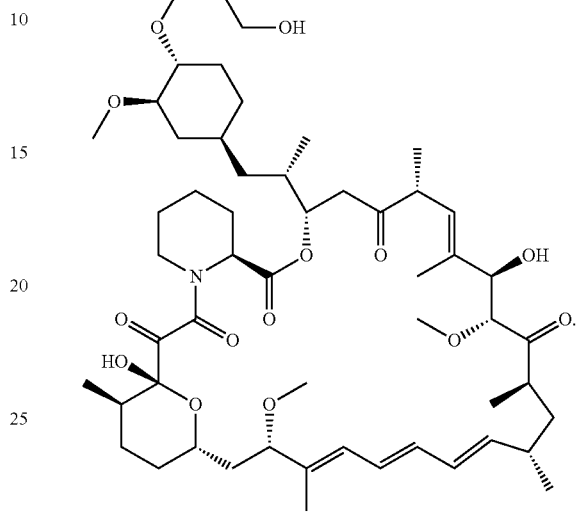

Disclosed herein, in certain instances, is A composition comprising: a therapeutically-effective amount of (S)—N-(3,4-difluoro-2-(2-fluoro-4-iodophenylamino)-6-methoxyphenyl)-1-(2,3-dihydroxypropyl)cyclopropane-1-sulfonamide, a salt thereof, or a polymorph thereof; and (1R,2R,4S)-4-{(2R)-2-[(3S,6R,7E,9R,10R,12R,14S,15E,17E,19E,21S,23S,26R,27R,34aS)-9,27-dihydroxy-10,21-dimethoxy-6,8,12,14,20,26-hexamethyl-1,5,11,28,29-pentaoxo-1,4,5,6,9,10,11,12,13,14,21,22,23,24,25,26,27,28,29,31,32,33,34,34a-tetracosahydro-3H-23,27-epoxypyrido[2,1-c][1,4]oxazacyclohentriacontin-3-yl]propyl}-2-methoxycyclohexyl 3-hydroxy-2-(hydroxymethyl)-2-methylpropanoate:

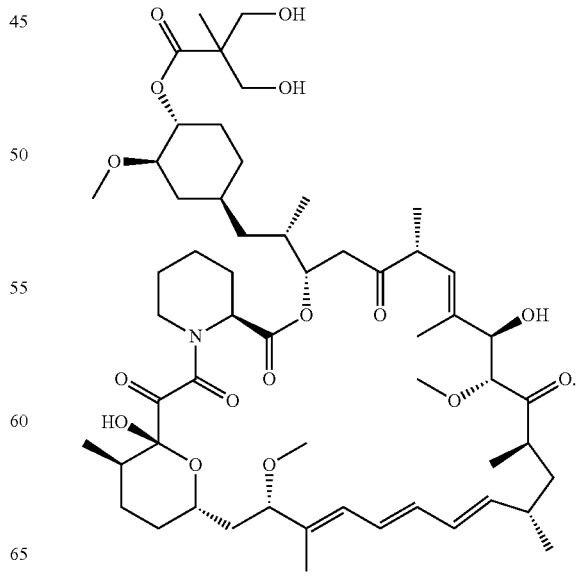

Disclosed herein, in certain instances, is a method of treating colon cancer, comprising administering to an individual in need thereof a synergistic combination of: a therapeutically-effective amount of (S)—N-(3,4-difluoro-2-(2-fluoro-4-iodophenylamino)-6-methoxyphenyl)-1-(2,3-dihydroxypropyl)cyclopropane-1-sulfonamide, a salt thereof, or a polymorph thereof; and an effective amount of dihydroxy-12-[(2R)-1-[(1S,3R,4R)-4-(2-hydroxyethoxy)-3-methoxycyclohexyl]propan-2-yl]-19,30-dimethoxy-15,17,21,23,29,35-hexamethyl-11,36-dioxa-4-azatricyclo[30.3.1.04,9]hexatriaconta-16,24,26,28-tetraene-2,3,10,14,20-pentone:

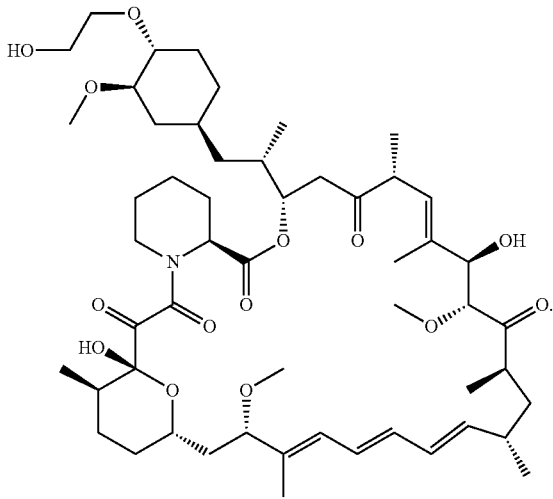 [SMILES: CO[C@H]1C[C@@H]2CC[C@@H](C)[C@@](O)(O2)C(=O)C(=O)N2CCCC[C@H]2C(=O)O[C@H]([C@@H](C)C[C@@H]2CC[C@@H](OCCO)[C@H](OC)C2)CC(=O)[C@H](C)/C=C(\C)[C@@H](O)[C@@H](OC)C(=O)[C@H](C)C[C@H](C)/C=C/C=C/C=C/1C]

Disclosed herein, in certain instances, is A composition comprising: (a therapeutically-effective amount of (S)—N-(3,4-difluoro-2-(2-fluoro-4-iodophenylamino)-6-methoxyphenyl)-1-(2,3-dihydroxypropyl)cyclopropane-1-sulfonamide, a salt thereof, or a polymorph thereof; and Dihydroxy-12-[(2R)-1-[(1S,3R,4R)-4-(2-hydroxyethoxy)-3-methoxycyclohexyl]propan-2-yl]-19,30-dimethoxy-15,17,21,23,29,35-hexamethyl-11,36-dioxa-4-azatricyclo[30.3.1.04,9]hexatriaconta-16,24,26,28-tetraene-2,3,10,14,20-pentone:

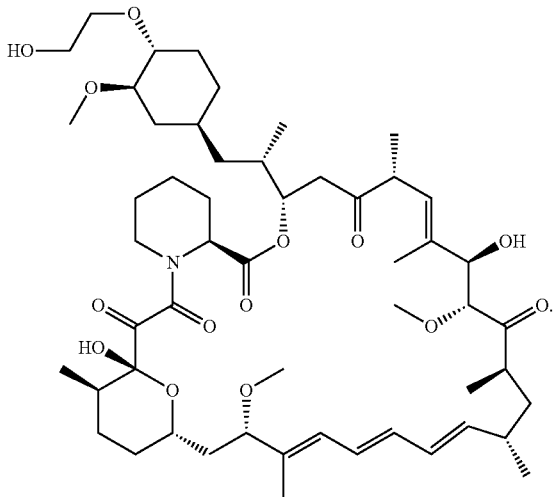 [SMILES: CO[C@H]1C[C@@H]2CC[C@@H](C)[C@@](O)(O2)C(=O)C(=O)N2CCCC[C@H]2C(=O)O[C@H]([C@@H](C)C[C@@H]2CC[C@@H](OCCO)[C@H](OC)C2)CC(=O)[C@H](C)/C=C(\C)[C@@H](O)[C@@H](OC)C(=O)[C@H](C)C[C@H](C)/C=C/C=C/C=C/1C]

In some embodiments, a composition disclosed herein further comprises a pharmaceutically acceptable carrier.

In some embodiments, a composition disclosed herein further comprises one or more additional chemotherapeutic agents.

Disclosed herein, in certain embodiments, is a kit for treating a subject having cancer, comprising: a composition disclosed herein; and instructions for administration of the composition to treat cancer.

In some embodiments, a method disclosed herein further comprises administering an additional therapy.

In some embodiments, a method disclosed herein further comprises administering radiation therapy.

In some embodiments, a method disclosed herein further comprises administering one or more additional chemotherapeutic agents.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION OF THE INVENTION

Figure 1:
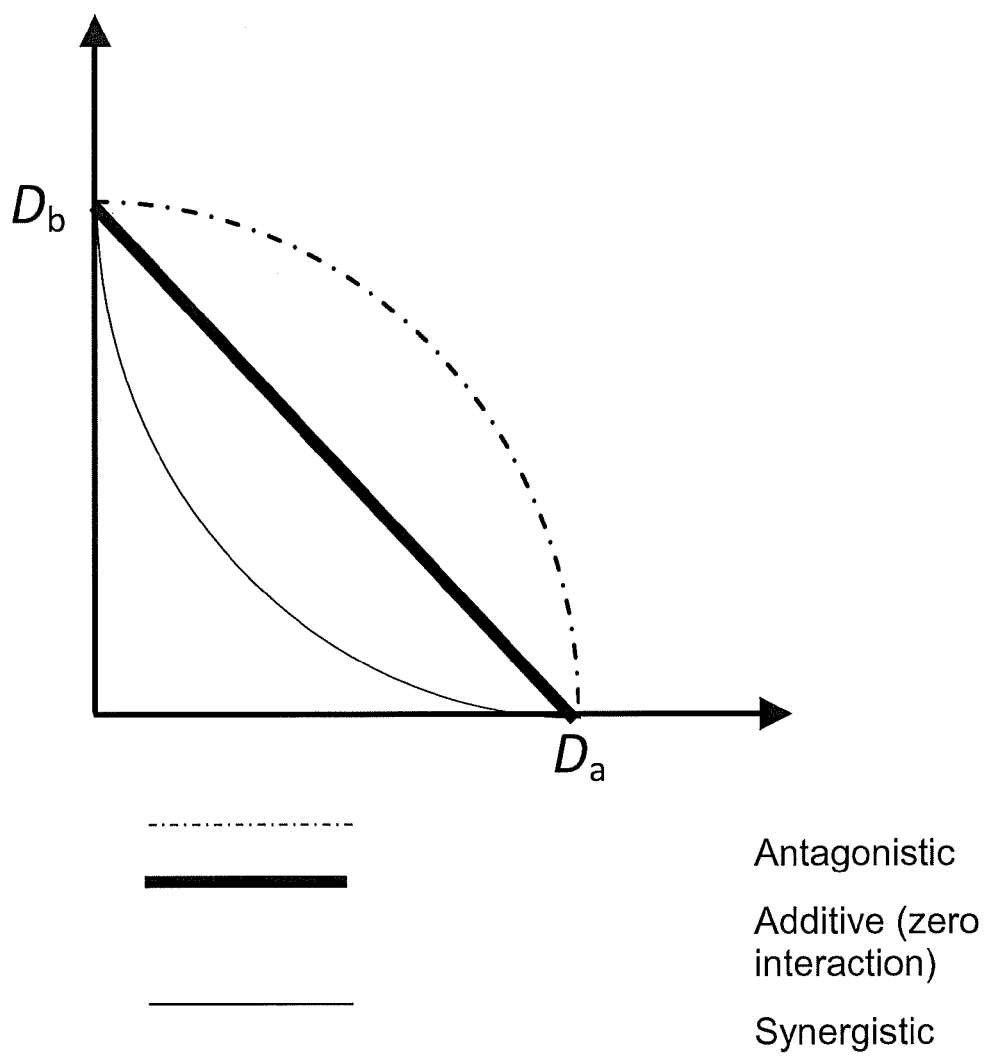
FIG. 1 shows a theoretical isobologram depicting curves for zero interaction between two drugs (additive effect only), negative interaction (antagonism) and positive interaction (synergy).
Figure 2:
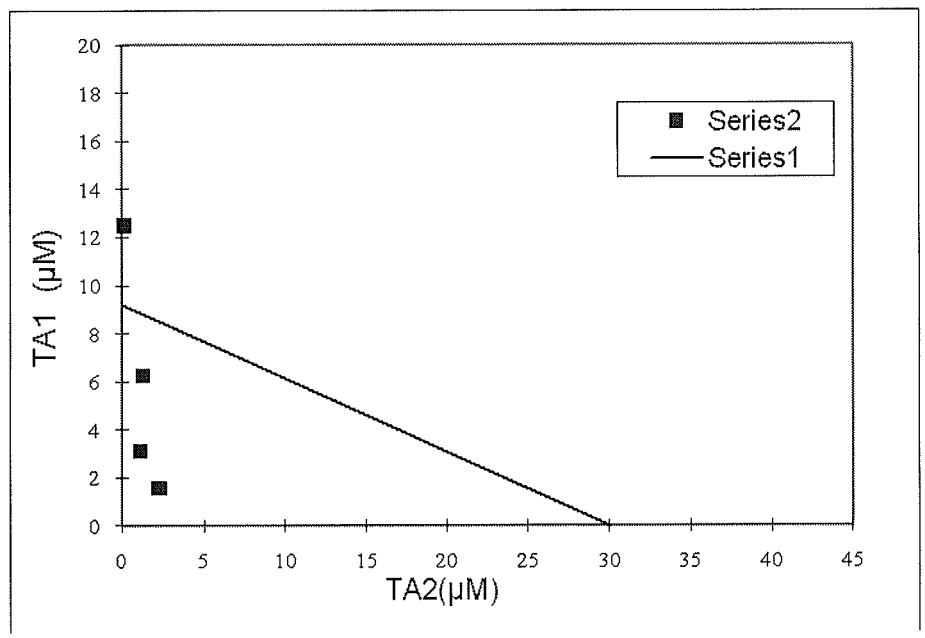
FIG. 2 shows isobolograms for TA1 with TA2 in A549 NSCLC cells.
Figure 2:
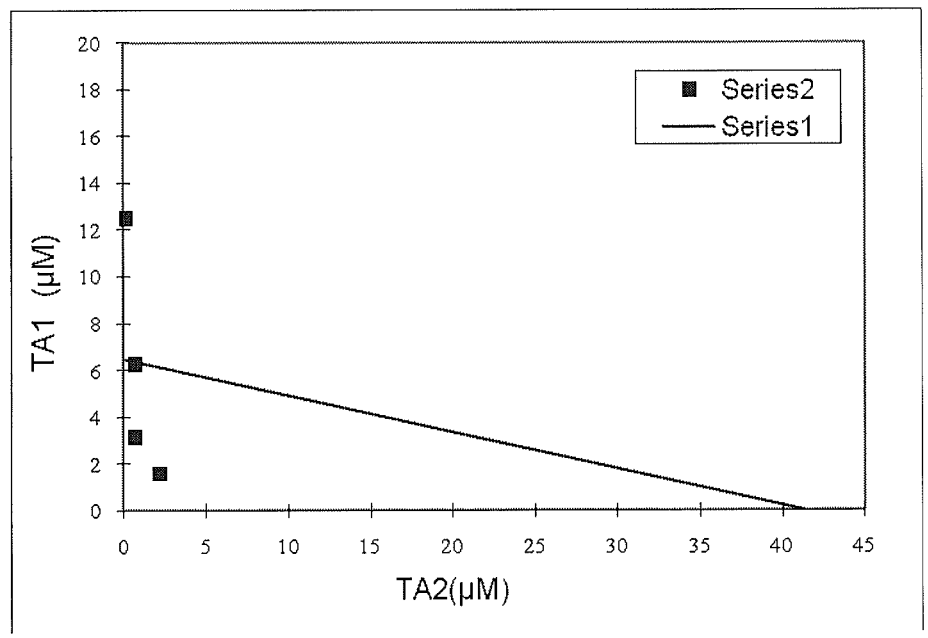
Figure 3:
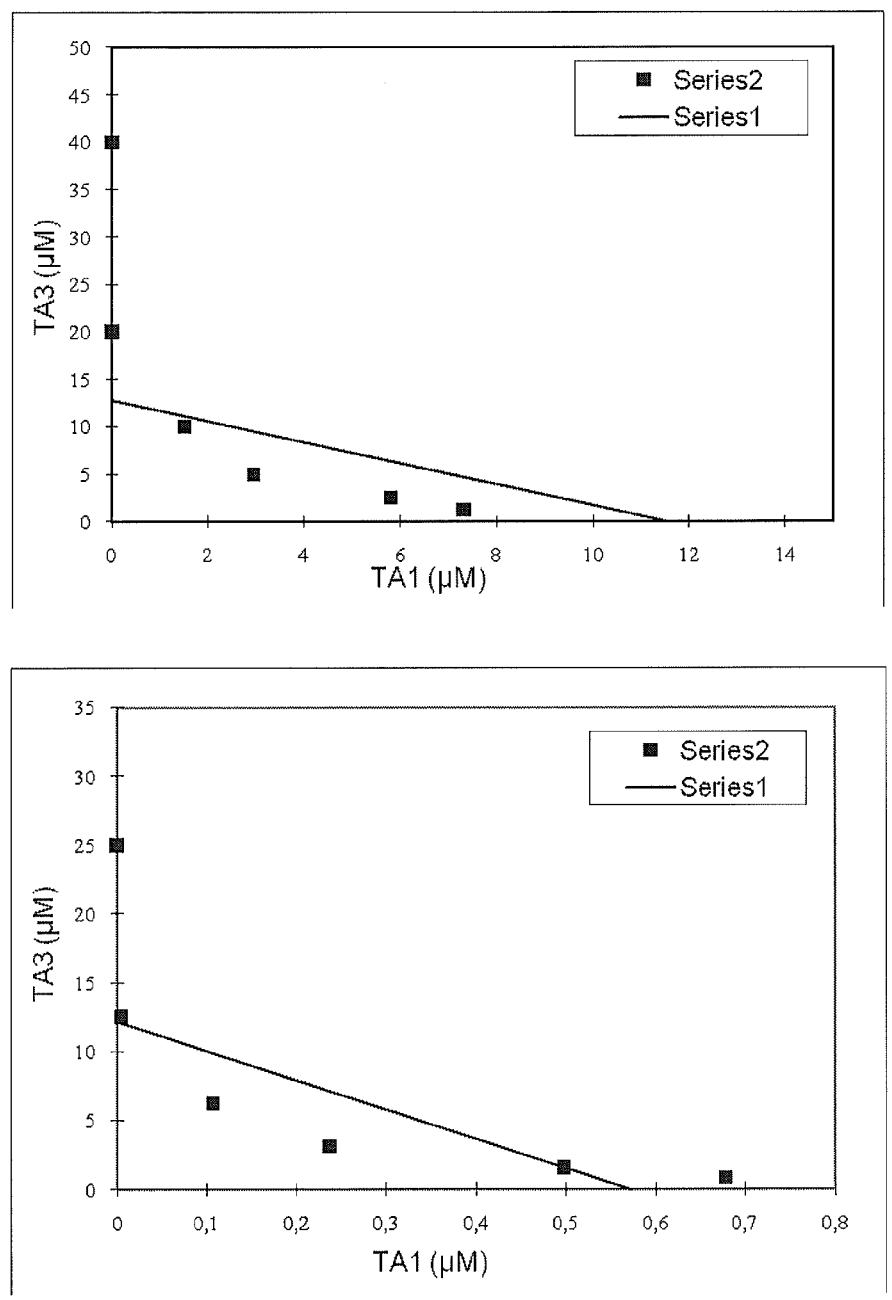
FIG. 3 shows isobolograms for TA1 with TA3 in A549 NSCLC cells.
Figure 4:
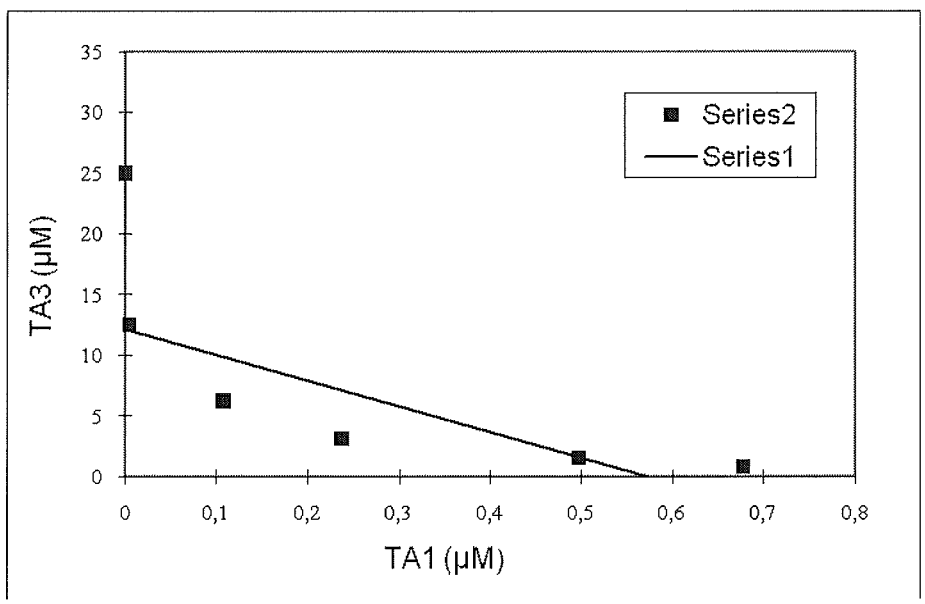
FIG. 4 shows isobolograms for TA1 with TA3 in MDA-MB231 breast cancer cells.
Figure 4:
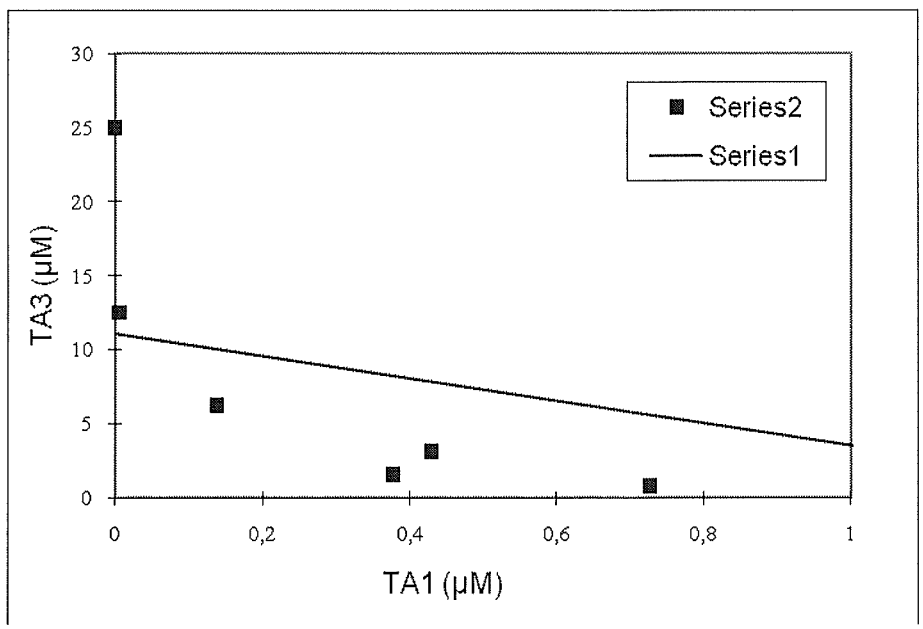
Figure 5:
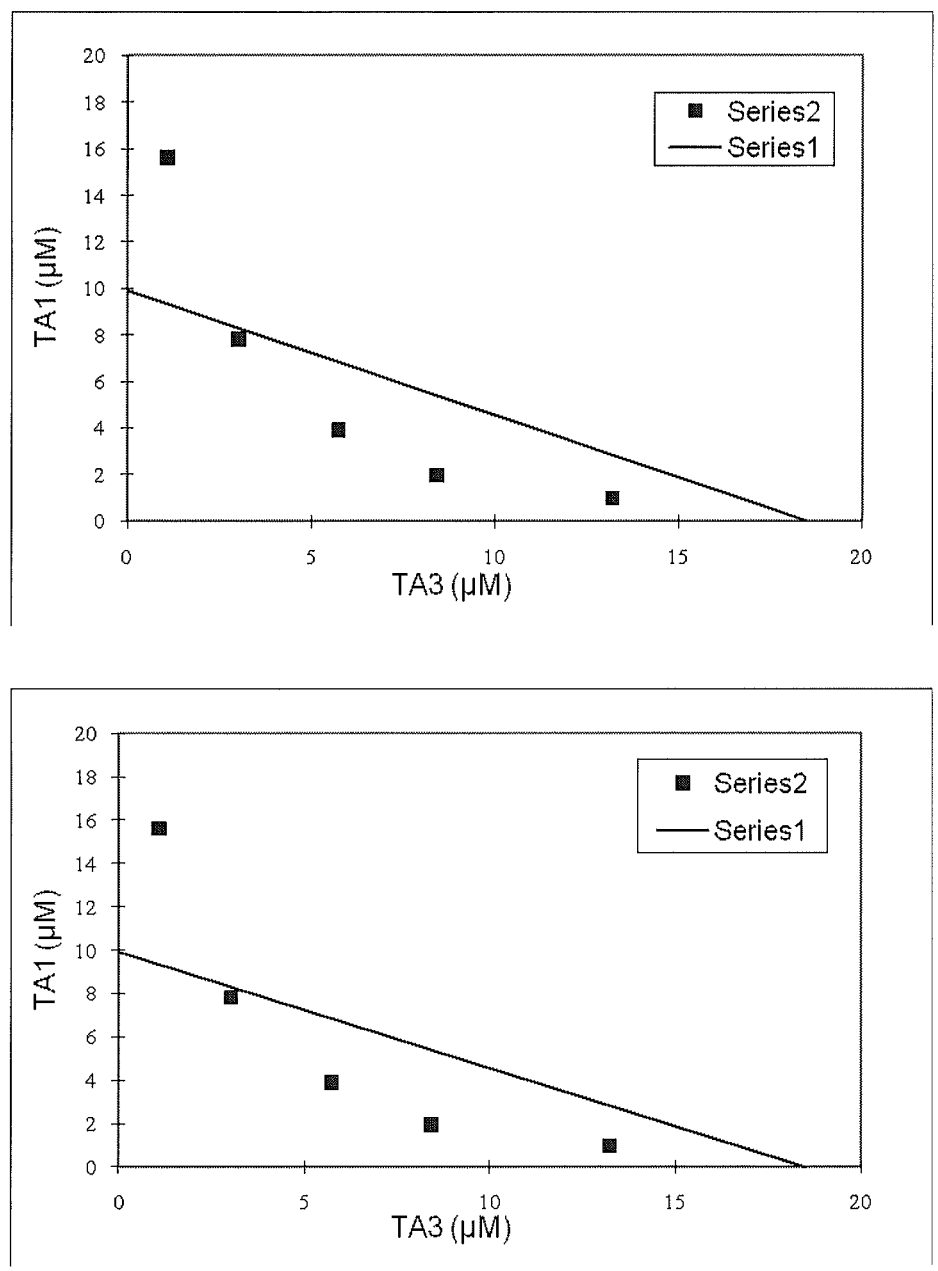
FIG. 5 shows isobolograms for TA1 with TA3 in SW579 thyroid cancer cells.
Figure 6:
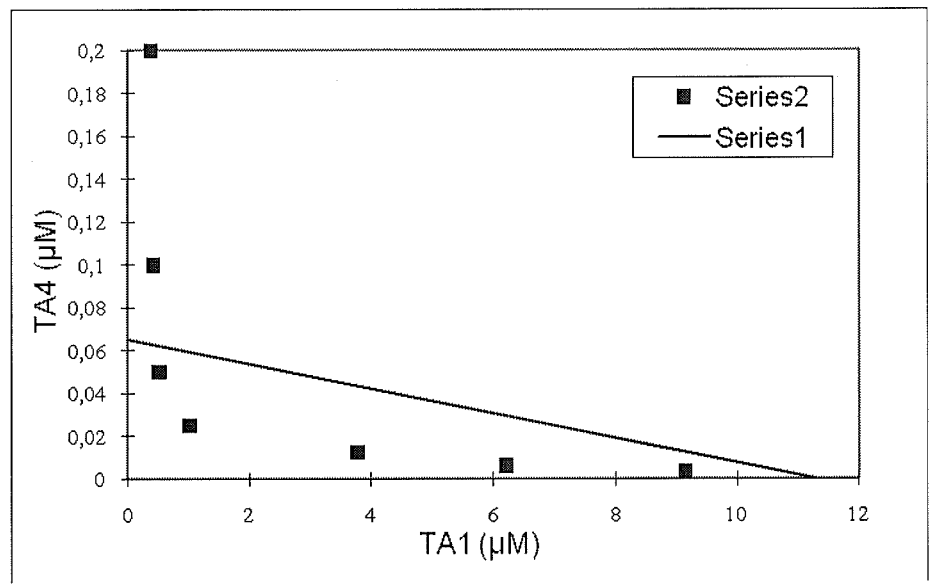
FIG. 6 shows isobolograms for TA1 with TA4 in NSCLC cells.
Figure 6:
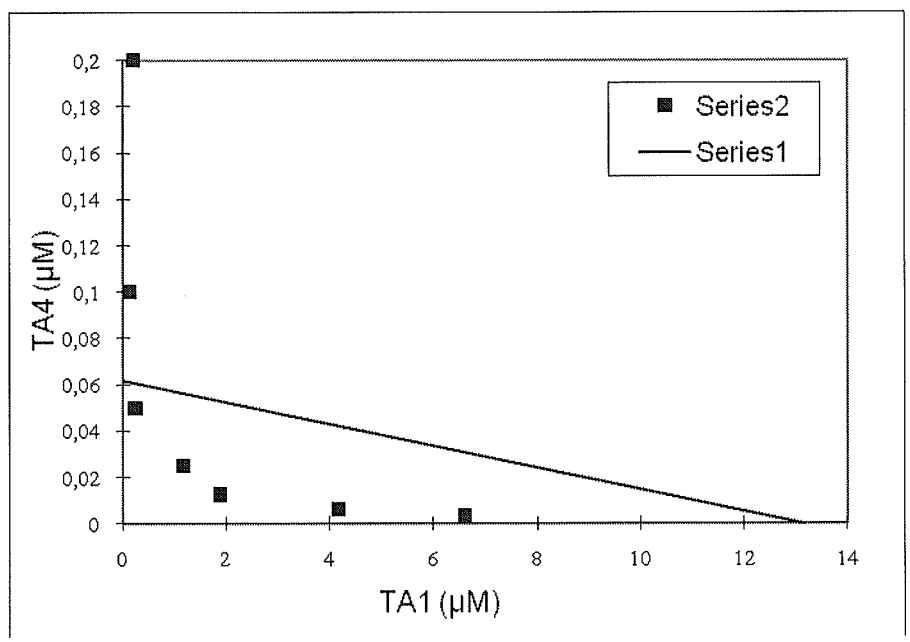
Figure 7:
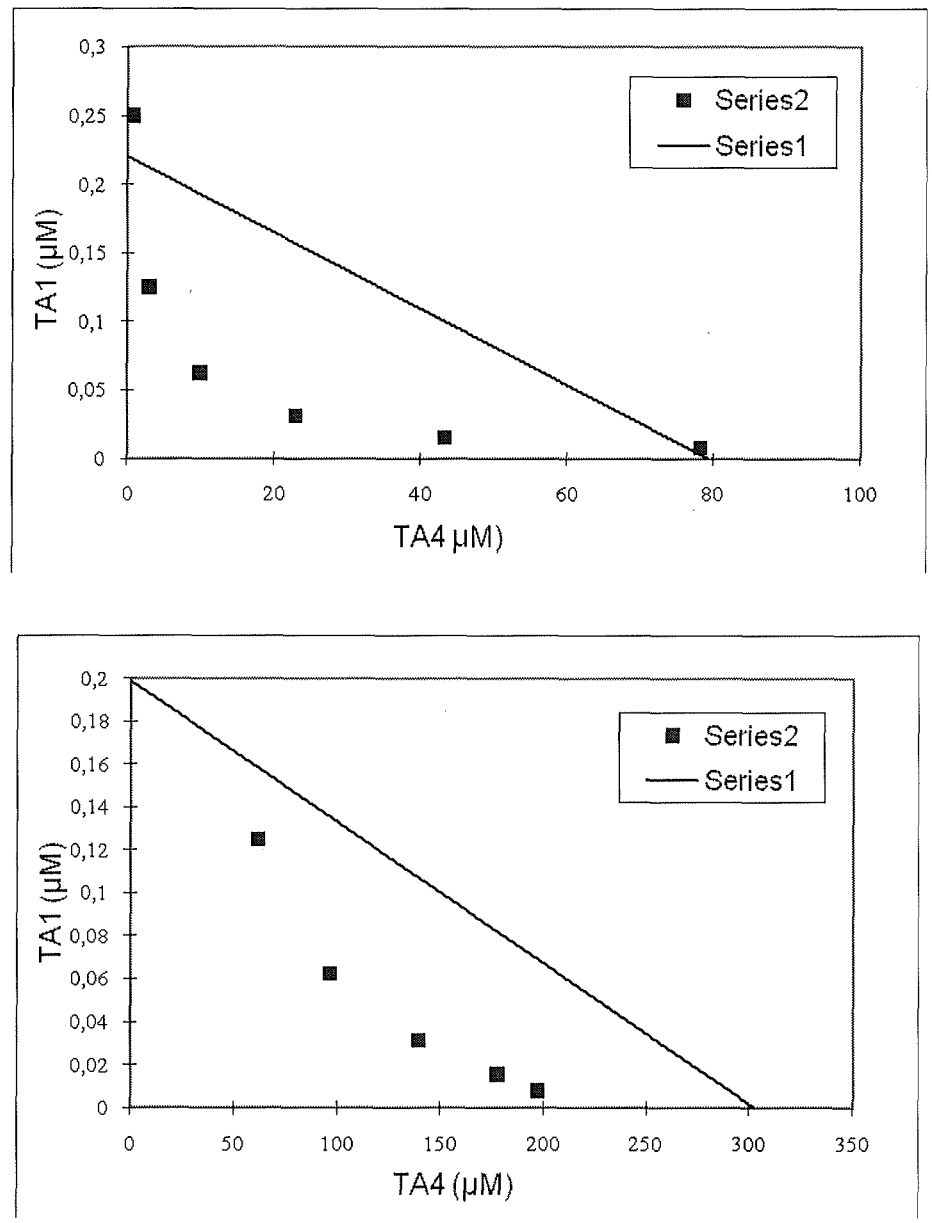
FIG. 7 shows isobolograms for TA1 with TA4 in G361 melanoma cells.
Figure 8:
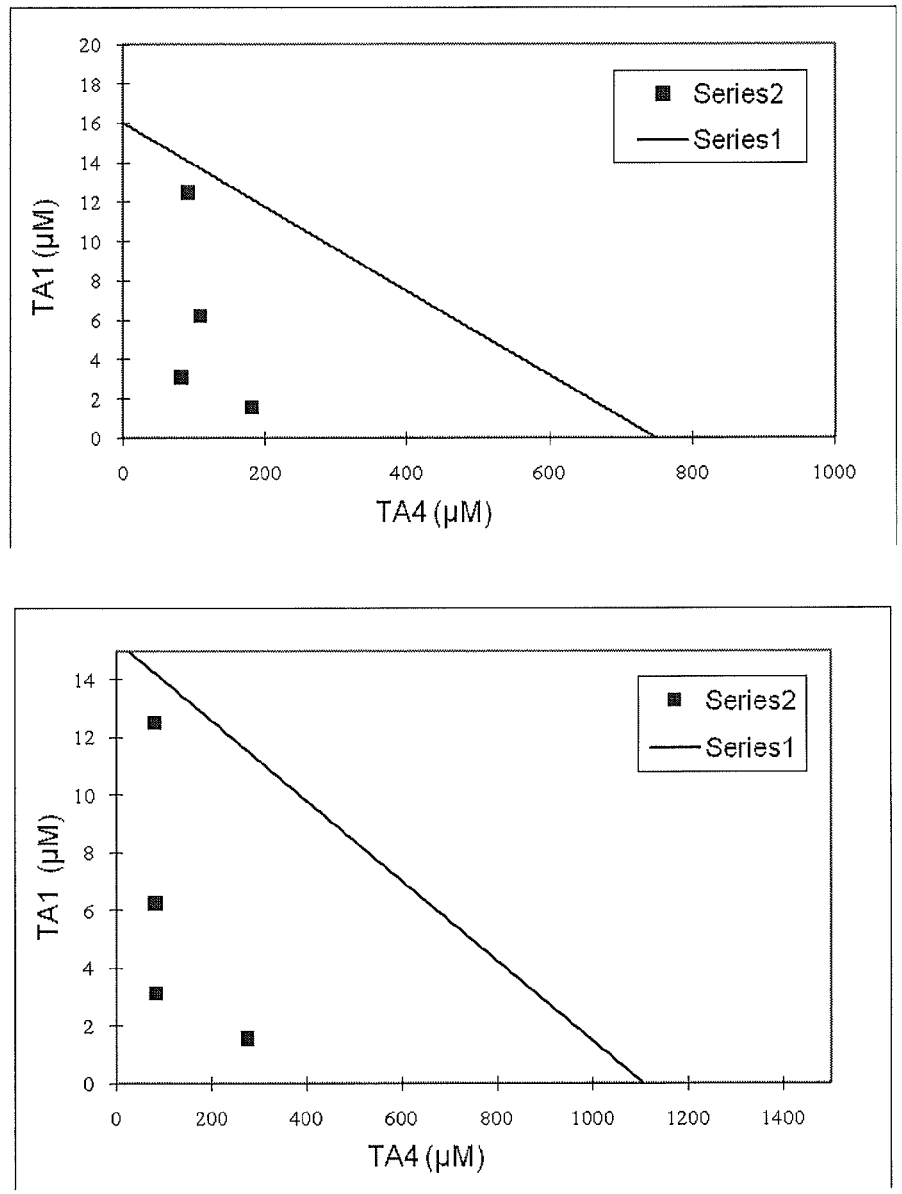
FIG. 8 shows isobolograms for TA1 with TA4 in MCF-7 human breast cancer cells.
Figure 9:
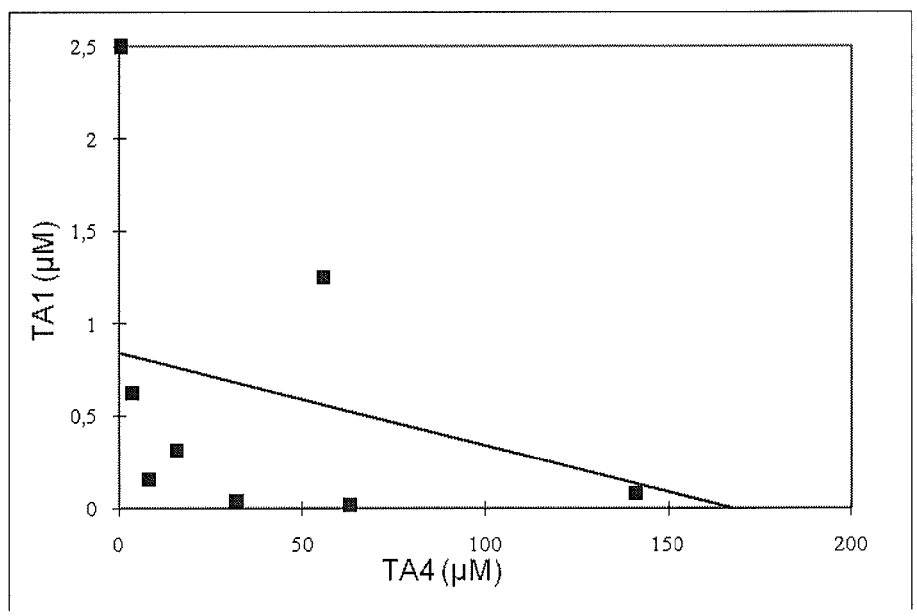
FIG. 9 shows isobolograms for TA1 with TA4 in Mia-PaCa-2 pancreatic cells.
Figure 9:
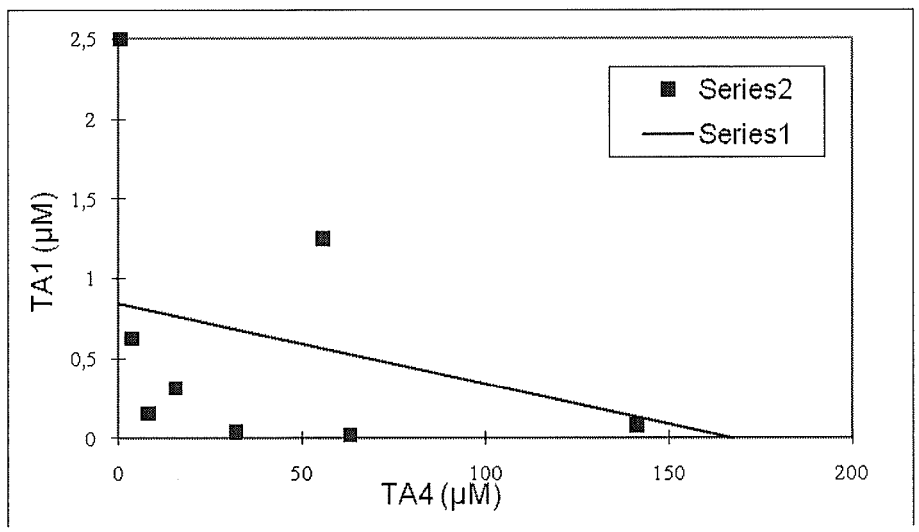
Figure 10:
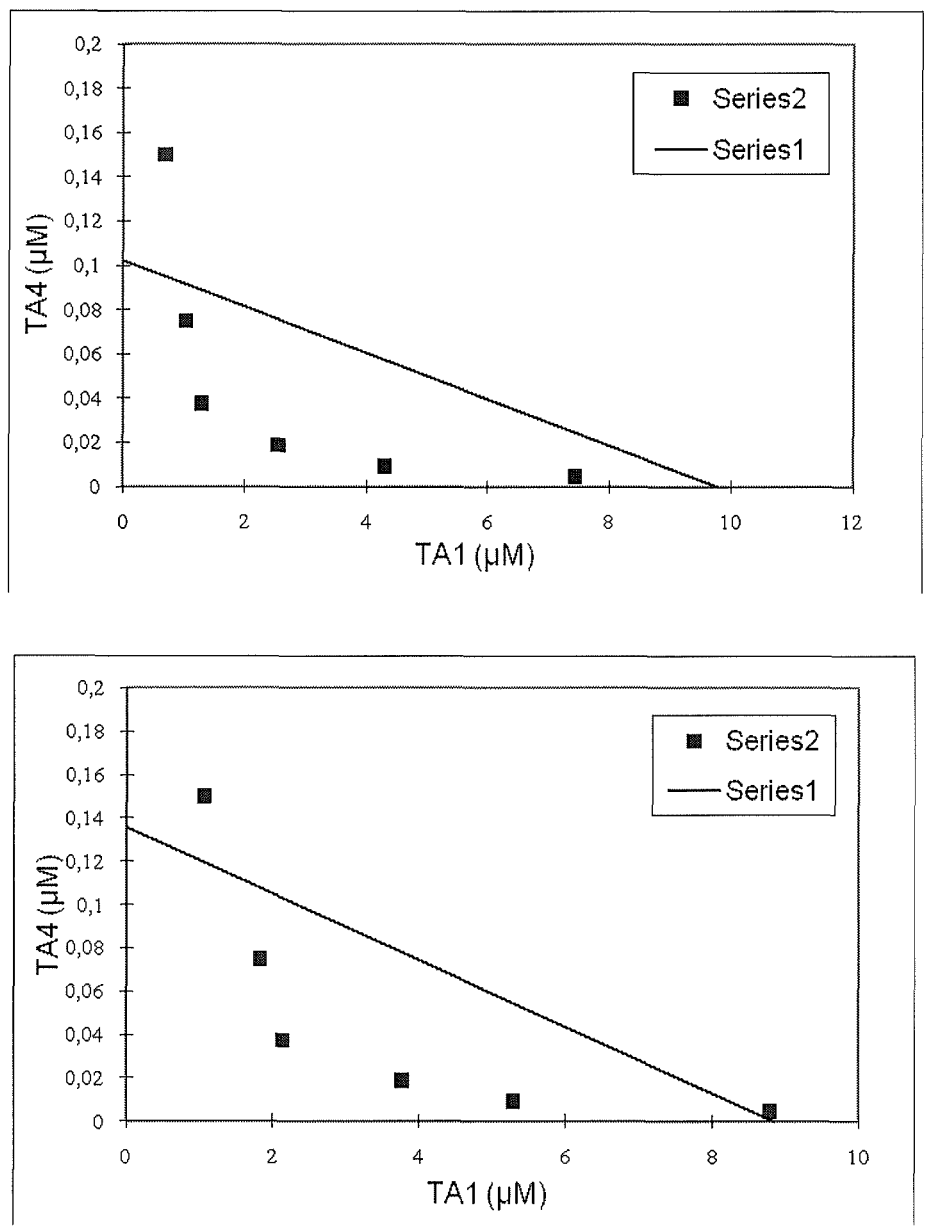
FIG. 10 shows isobolograms for TA1 with TA4 in SW579 thyroid cancer cells.
Figure 11:
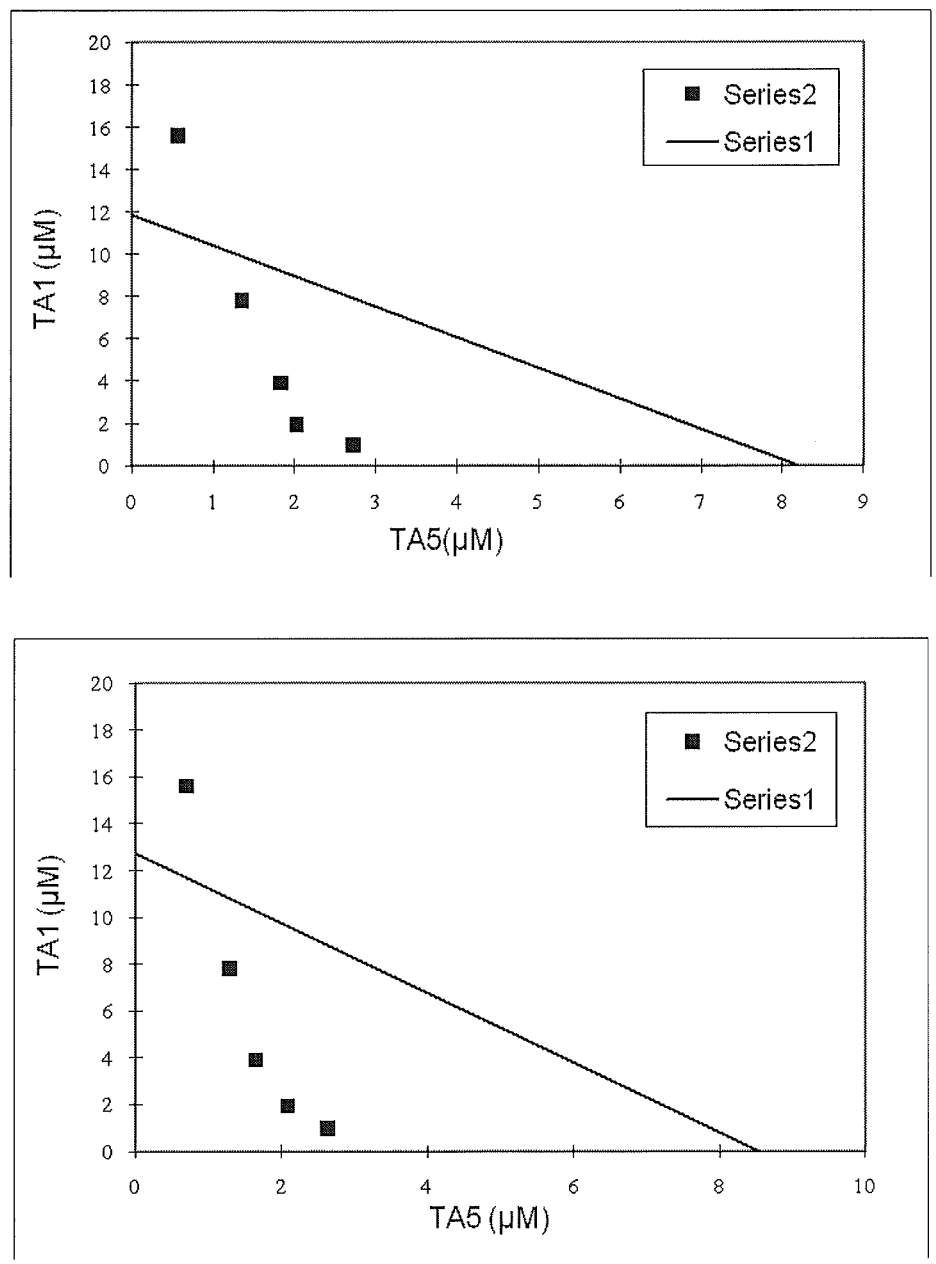
FIG. 11 shows isobolograms for TA1 with TA5 in SW579 thyroid cancer cells.
Figure 12:
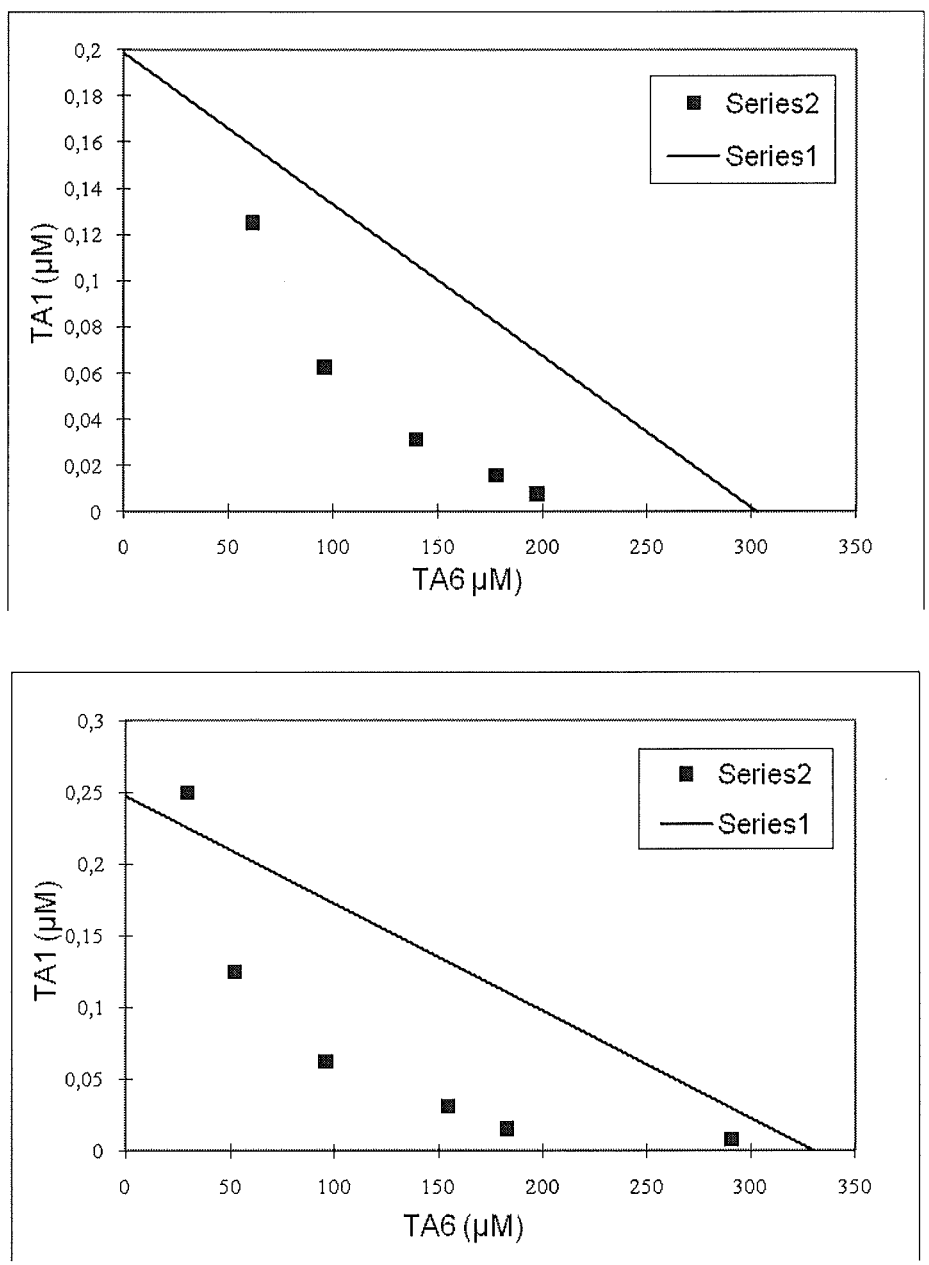
FIG. 12 shows isobolograms for TA1 with TA6 in G361 melanoma cells.
Figure 13:
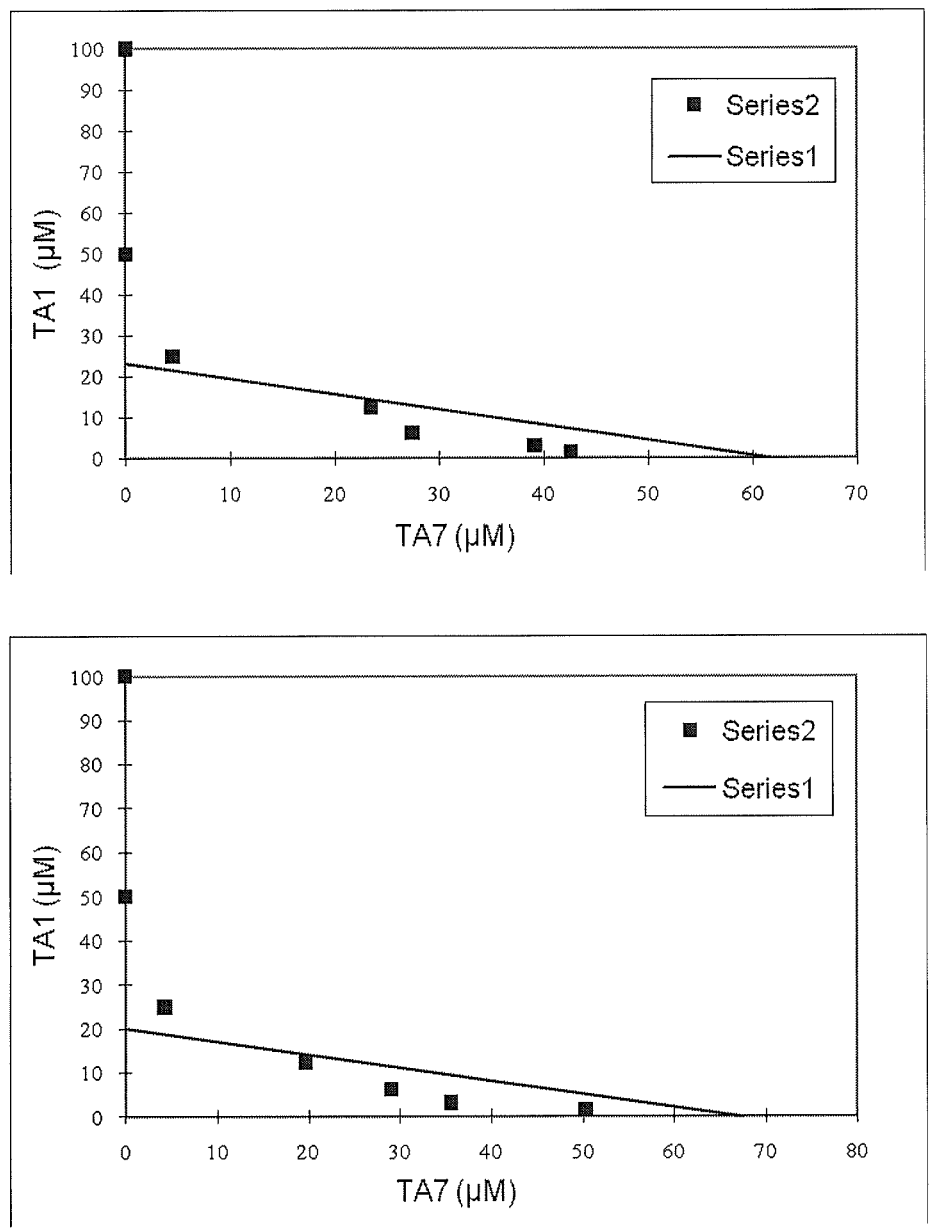
FIG. 13 shows isobolograms for TA1 with TA7 in MCF-7 breast cancer cells.
Figure 14:
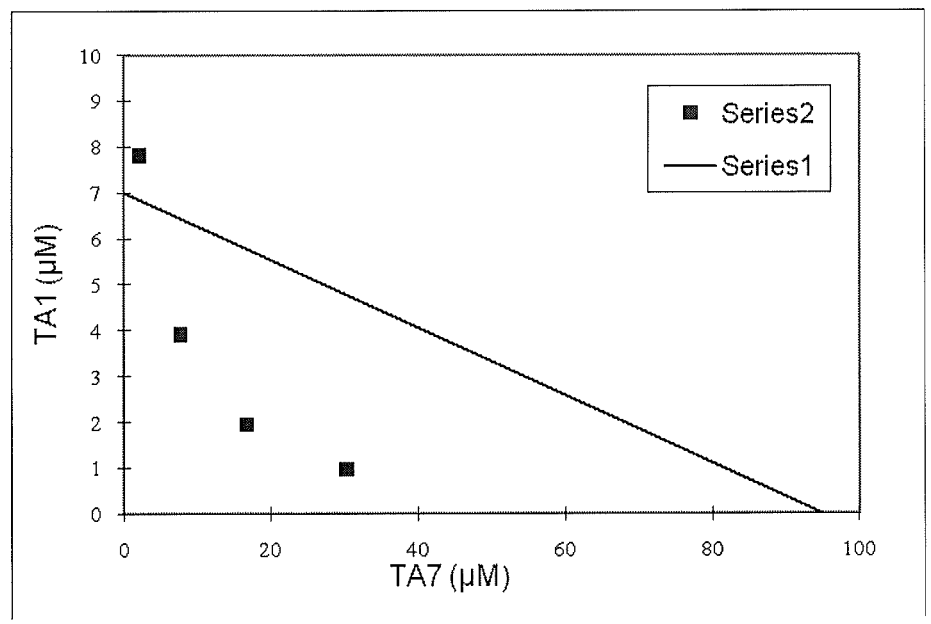
FIG. 14 shows isobolograms for TA1 with TA7 in SW579 thyroid cancer cells.
Figure 14:
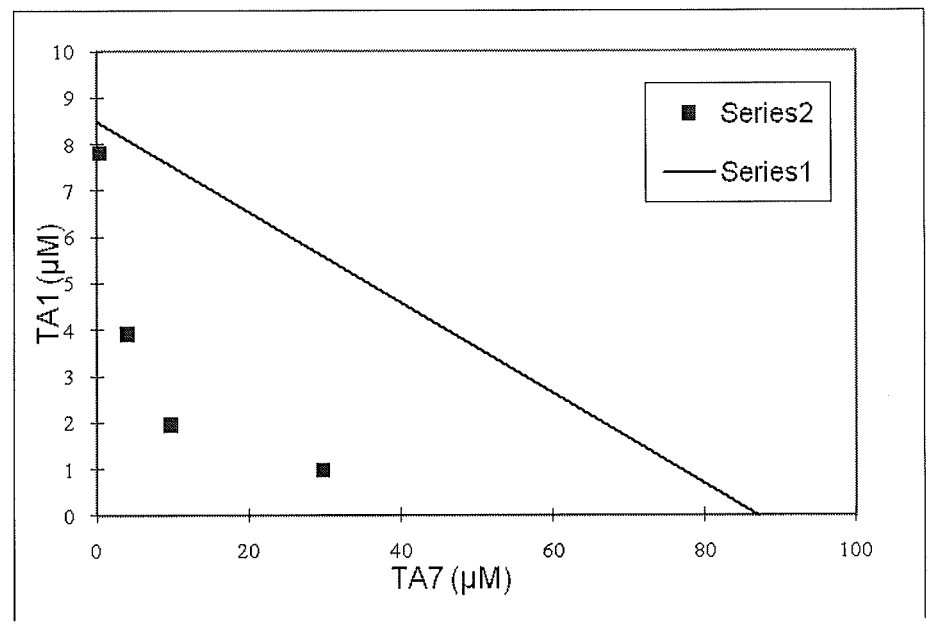

Described herein are compositions and methods for treating specific cancers comprising a synergistic combination of (S)—N-(3,4-difluoro-2-(2-fluoro-4-iodophenylamino)-6- methoxyphenyl)-1-(2,3-dihydroxypropyl)cyclopropane-1-sulfonamide and a second anticancer agent.

(S)—N-(3,4-difluoro-2-(2-fluoro-4-iodophenylamino)-6-methoxyphenyl)-1-(2,3-dihydroxypropyl)cyclopropane-1-sulfonamide has been described previously (see for example international patent application WO/2007/014011 or US 2008-0058340).

DEFINITIONS

The terms "individual," "individual," or "subject" are used interchangeably. As used herein, they mean any mammal (i.e. species of any orders, families, and genus within the taxonomic classification animalia: chordata: vertebrata: mammalia). In some embodiments, the mammal is a human. In some embodiments, the mammal is a non-human. In some embodiments, the mammal is a member of the taxonomic orders: primates (e.g. lemurs, lorids, galagos, tarsiers, monkeys, apes, and humans); rodentia (e.g. mice, rats, squirrels, chipmunks, and gophers); lagomorpha (e.g. hares, rabbits, and pika); erinaceomorpha (e.g. hedgehogs and gymnures); soricomorpha (e.g. shrews, moles, and solenodons); chiroptera (e.g., bats); cetacea (e.g. whales, dolphins, and porpoises); carnivora (e.g. cats, lions, and other feliformia; dogs, bears, weasels, and seals); perissodactyla (e.g. horse, zebra, tapir, and rhinoceros); artiodactyla (e.g. pigs, camels, cattle, and deer); proboscidea (e.g. elephants); sirenia (e.g. manatees, dugong, and sea cows); cingulata (e.g. armadillos); pilosa (e.g. anteaters and sloths); didelphimorphia (e.g. american opossums); paucituberculata (e.g. shrew opossums); microbiotheria (e.g. Monito del Monte); notoryctemorphia (e.g. marsupial moles); dasyuromorphia (e.g. marsupial carnivores); peramelemorphia (e.g. bandicoots and bilbies); or diprotodontia (e.g. wombats, koalas, possums, gliders, kangaroos, wallaroos, and wallabies). In some embodiments, the animal is a reptile (i.e. species of any orders, families, and genus within the taxonomic classification animalia: chordata: vertebrata: reptilia). In some embodiments, the animal is a bird (i.e. animalia: chordata: vertebrata: ayes). None of the terms require or are limited to situation characterized by the supervision (e.g. constant or intermittent) of a health care worker (e.g. a doctor, a registered nurse, a nurse practitioner, a physician's assistant, an orderly, or a hospice worker).

The terms "treat," "treating" or "treatment," and other grammatical equivalents as used herein, include alleviating, inhibiting or reducing symptoms, reducing or inhibiting severity of, reducing incidence of, prophylactic treatment of, reducing or inhibiting recurrence of, preventing, delaying onset of, delaying recurrence of, abating or ameliorating a disease or condition symptoms, ameliorating the underlying metabolic causes of symptoms, inhibiting the disease or condition, e.g., arresting the development of the disease or condition, relieving the disease or condition, causing regression of the disease or condition, relieving a condition caused by the disease or condition, or stopping the symptoms of the disease or condition. The terms further include achieving a therapeutic benefit. By therapeutic benefit is meant eradication or amelioration of the underlying disorder being treated, and/or the eradication or amelioration of one or more of the physiological symptoms associated with the underlying disorder such that an improvement is observed in the individual.

The terms "prevent," "preventing" or "prevention," and other grammatical equivalents as used herein, include preventing additional symptoms, preventing the underlying metabolic causes of symptoms, inhibiting the disease or condition, e.g., arresting the development of the disease or condition and are intended to include prophylaxis. The terms further include achieving a prophylactic benefit. For prophylactic benefit, the compositions are optionally administered to an individual at risk of developing a particular disease, to an individual reporting one or more of the physiological symptoms of a disease, or to an individual at risk of reoccurrence of the disease.

Where combination treatments or prevention methods are contemplated, it is not intended that the agents described herein be limited by the particular nature of the combination. For example, the agents described herein are optionally administered in combination as simple mixtures as well as chemical hybrids. An example of the latter is where the agent is covalently linked to a targeting carrier or to an active pharmaceutical. Covalent binding can be accomplished in many ways, such as, though not limited to, the use of a commercially available cross-linking agent. Furthermore, combination treatments are optionally administered separately or concomitantly.

As used herein, the terms "pharmaceutical combination", "administering an additional therapy", "administering an additional therapeutic agent" and the like refer to a pharmaceutical therapy resulting from the mixing or combining of more than one active ingredient and includes both fixed and non-fixed combinations of the active ingredients. The term "fixed combination" means that at least one of the agents described herein, and at least one co-agent, are both administered to an individual simultaneously in the form of a single entity or dosage. The term "non-fixed combination" means that at least one of the agents described herein, and at least one co-agent, are administered to an individual as separate entities either simultaneously, concurrently or sequentially with variable intervening time limits, wherein such administration provides effective levels of the two or more agents in the body of the individual. In some instances, the co-agent is administered once or for a period of time, after which the agent is administered once or over a period of time. In other instances, the co-agent is administered for a period of time, after which, a therapy involving the administration of both the co-agent and the agent are administered. In still other embodiments, the agent is administered once or over a period of time, after which, the co-agent is administered once or over a period of time. These also apply to cocktail therapies, e.g. the administration of three or more active ingredients.

As used herein, the terms "co-administration", "administered in combination with" and their grammatical equivalents are meant to encompass administration of the selected therapeutic agents to a single individual, and are intended to include treatment regimens in which the agents are administered by the same or different route of administration or at the same or different times. In some embodiments the agents described herein will be co-administered with other agents. These terms encompass administration of two or more agents to an animal so that both agents and/or their metabolites are present in the animal at the same time. They include simultaneous administration in separate compositions, administration at different times in separate compositions, and/or administration in a composition in which both agents are present. Thus, in some embodiments, the agents described herein and the other agent(s) are administered in a single composition. In some embodiments, the agents described herein and the other agent(s) are admixed in the composition.

The terms "effective amount" or "therapeutically effective amount" as used herein, refer to a sufficient amount of at least one agent being administered which achieve a desired result, e.g., to relieve to some extent one or more symptoms of a disease or condition being treated. In certain instances, the result is a reduction and/or alleviation of the signs, symptoms, or causes of a disease, or any other desired alteration of a biological system. In specific instances, the result is a decrease in the growth of, the killing of, or the inducing of apoptosis in at least one abnormally proliferating cell, e.g., a cancer stem cell. In certain instances, an "effective amount" for therapeutic uses is the amount of the composition comprising an agent as set forth herein required to provide a clinically significant decrease in a disease. An appropriate "effective" amount in any individual case is determined using any suitable technique, such as a dose escalation study.

The terms "administer," "administering", "administration," and the like, as used herein, refer to the methods that may be used to enable delivery of agents or compositions to the desired site of biological action. These methods include, but are not limited to oral routes, intraduodenal routes, parenteral injection (including intravenous, subcutaneous, intraperitoneal, intramuscular, intravascular or infusion), topical and rectal administration. Administration techniques that are optionally employed with the agents and methods described herein, include e.g., as discussed in Goodman and Gilman, The Pharmacological Basis of Therapeutics, current ed.; Pergamon; and Remington's, Pharmaceutical Sciences (current edition), Mack Publishing Co., Easton, Pa. In certain embodiments, the agents and compositions described herein are administered orally.

The term "pharmaceutically acceptable" as used herein, refers to a material that does not abrogate the biological activity or properties of the agents described herein, and is relatively nontoxic (i.e., the toxicity of the material significantly outweighs the benefit of the material). In some instances, a pharmaceutically acceptable material may be administered to an individual without causing significant undesirable biological effects or significantly interacting in a deleterious manner with any of the components of the composition in which it is contained.

As used herein, the terms "synergy," "synergistically," "synergistic" or other grammatical equivalents thereof mean an interaction of two or more compounds such that the effect is additive (i.e., the effect of the two compounds is greater than either individually) or that the addition of one compound results in less of the other compound being required. In some embodiments, the co-administration of (a) (S)—N-(3,4-difluoro-2-(2-fluoro-4-iodophenylamino)-6-methoxyphenyl)-1-(2,3-dihydroxypropyl)cyclopropane-1-sulfonamide, a salt thereof, or a polymorph thereof (see e.g., U.S. application Ser. No. 12/399,848); results in the need for a smaller dose of a second active agent. In some embodiments, the co-administration of a second active agent and (S)—N-(3,4-difluoro-2-(2-fluoro-4-iodophenylamino)-6-methoxyphenyl)-1-(2,3-dihydroxypropyl)cyclopropane-1-sulfonamide, a salt thereof, or a polymorph thereof (see e.g., U.S. application Ser. No. 12/399,848) results in the need for a smaller dose of (S)—N-(3,4-difluoro-2-(2-fluoro-4-iodophenylamino)-6-methoxyphenyl)-1-(2,3-dihydroxypropyl)cyclopropane-1-sulfonamide.

Combination Therapies

Disclosed herein, in certain embodiments, are methods and pharmaceutical compositions for modulating a cancer comprising a synergistic combination of (a) a therapeutically-effective amount of (S)—N-(3,4-difluoro-2-(2-fluoro-4-iodophenylamino)-6-methoxyphenyl)-1-(2,3-dihydroxypropyl)cyclopropane-1-sulfonamide, a salt thereof, or a polymorph thereof (see e.g., U.S. application Ser. No. 12/399,848); and (b) a second active agent selected from an agent that treats cancer. In some embodiments, the second active agent is selected from an agent disclosed in Table 1.

TABLE 1

| | |
|---|---|
| 3-(6,7-bis(2-methoxyethoxy)quinazolin-4-ylamino)benzonitrile | 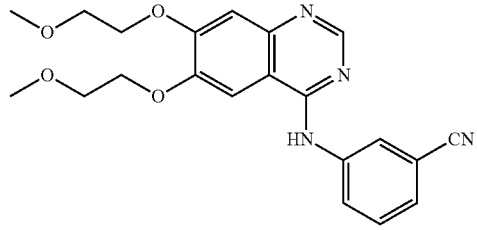 [SMILES: COCCOc1cc2ncnc(Nc3cccc(C#N)c3)c2cc1OCCOC] |
| N-(3-chloro-4-fluorophenyl)-7-methoxy-6-(3-morpholinopropoxy)quinazolin-4-amine | 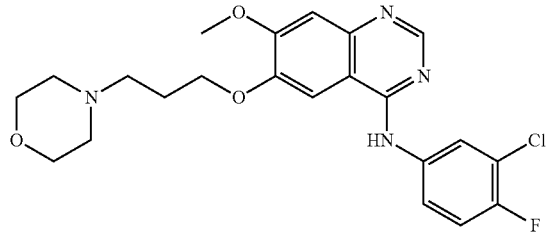 [SMILES: COc1cc2ncnc(Nc3ccc(F)c(Cl)c3)c2cc1OCCCN1CCOCC1] |
| 4-amino-1-[3,3-difluoro-4-hydroxy-5-(hydroxymethyl)tetrahydrofuran-2-yl]-1H-pyrimidin-2-one | 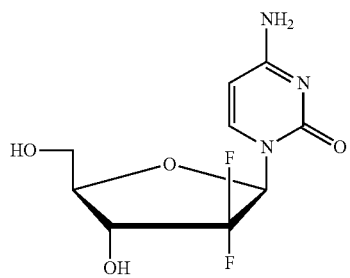 |

TABLE 1-continued

N-hydroxy-N'-phenyl-octanediamide

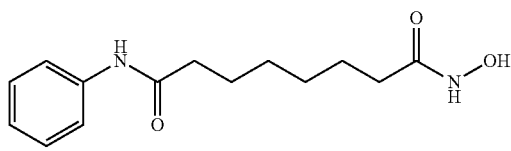 [SMILES: O=C(CCCCCCC(=O)Nc1ccccc1)NO]

4-methyl-5-oxo-2,3,4,6,8-pentazabicyclo[4.3.0]nona-2,7,9-triene-9-carboxamide

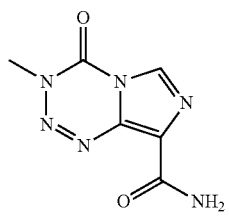

N-[3-chloro-4-[(3-fluorophenyl)methoxy]phenyl]-6-[5-[(2-methylsulfonylethylamino)methyl]-2-furyl]quinazolin-4-amine

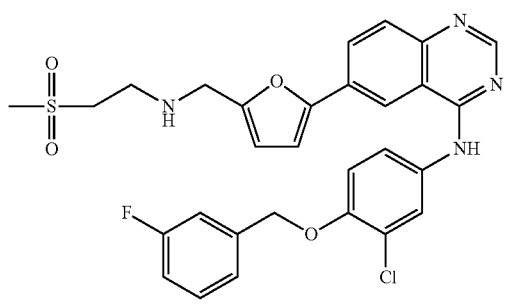 [SMILES: CS(=O)(=O)CCNCc1ccc(-c2ccc3ncnc(Nc4ccc(OCc5cccc(F)c5)c(Cl)c4)c3c2)o1]

(1R,2R,4S)-4-{(2R)-2-[(3S,6R,7E,9R,10R,12R,14S,15E,17E,19E,21S,23S,26R,27R,34aS)-9,27-dihydroxy-10,21-dimethoxy-6,8,12,14,20,26-hexamethyl-1,5,11,28,29-pentaoxo-1,4,5,6,9,10,11,12,13,14,21,22,23,24,25,26,27,28,29,31,32,33,34,34a-tetracosahydro-3H-23,27-epoxypyrido[2,1-c][1,4]oxazacyclohentriacontin-3-yl]propyl}-2-methoxycyclohexyl 3-hydroxy-2-(hydroxymethyl)-2-methylpropanoate

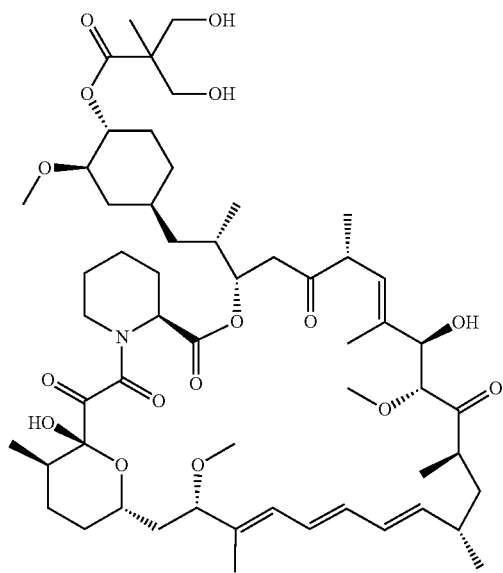 [SMILES: CO[C@H]1C[C@@H]2CC[C@@H](C)[C@@](O)(O2)C(=O)C(=O)N2CCCC[C@H]2C(=O)O[C@H]([C@@H](C)C[C@@H]2CC[C@@H](OC(=O)C(C)(CO)CO)[C@H](OC)C2)CC(=O)[C@H](C)/C=C(\C)[C@@H](O)[C@@H](OC)C(=O)[C@H](C)C[C@H](C)/C=C/C=C/C=C/1C]

TABLE 1-continued

| Dihydroxy-12-[(2R)-1-[(1S,3R,4R)-4-(2-hydroxyethoxy)-3-methoxycyclohexyl]propan-2-yl]-19,30-dimethoxy-15,17,21,23,29,35-hexamethyl-11,36-dioxa-4-azatricyclo[30.3.1.04,9]hexatriaconta-16,24,26,28-tetraene-2,3,10,14,20-pentone | 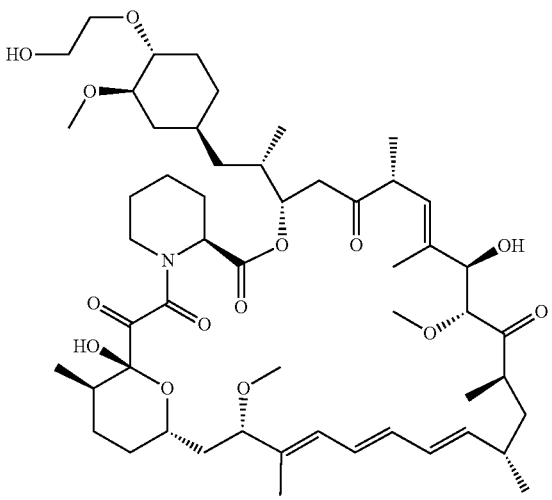 [SMILES: CO[C@H]1C[C@@H]2CC[C@@H](C)[C@@](O)(O2)C(=O)C(=O)N2CCCC[C@H]2C(=O)O[C@H]([C@@H](C)C[C@@H]2CC[C@@H](OCCO)[C@H](OC)C2)CC(=O)[C@H](C)/C=C(\C)[C@@H](O)[C@@H](OC)C(=O)[C@H](C)C[C@H](C)/C=C/C=C/C=C/1C] |

It is difficult to predict the effect of many combination therapies. For example, some drugs interact with each other to reduce therapeutic effectiveness or cause undesired side-effects. These drugs are typically categorized as having an antagonistic effect. Other drug combinations manifest their therapeutic effectiveness as the sum of individual drugs. These combinations are categorized as having an additive effect. Still other drug combinations result in a therapeutic index that is greater than the sum of individual drugs. These are categorized as having a synergistic effect.

Combination therapies having a synergistic effect are highly desirable for many reasons. For example, each component in the synergistic combination therapy can be used in an amount lower than the therapeutic amount of each individual drug in monotherapy (i.e., single drug administration). Moreover, the risk and/or the severity of side-effects can be reduced significantly by reducing the amount of each drug. Furthermore, combination therapy may significantly increase the overall effectiveness of treatment.

Synergistic actions of combination therapy are particularly useful in treatments where the side-effects are extreme or severe and/or where the efficacy of monotherapy is less than desirable. For example, cancer treatment often results in nausea, vomiting, bone marrow suppression, and other severe discomfort to the patient.

The nature of proliferative diseases like solid tumor diseases is multifactorial. In some aspects, drugs with different mechanisms of action may be combined. However, it should be noted that combining drugs with different modes of action does not necessarily lead to combinations with advantageous effects. In some instances, drugs within the same class may not have the same effect when used in combination.

Therapeutic synergy represents a therapeutic effect achieved with a tolerated regimen of a combination treatment that exceeds the optimal effect achieved at any tolerated dose of monotherapy associated with the same drugs used in the combination.

In some embodiments, a compound disclosed herein is administered in combination with surgery, and/or radiation therapy.

Salts (S)—N-(3,4-difluoro-2-(2-fluoro-4-iodophenylamino)-6-methoxyphenyl)-1-(2,3-dihydroxypropyl)cyclopropane-1-sulfonamide may form salts which are also within the scope of this invention. In some embodiments, the salts are pharmaceutically acceptable salts (i.e. non-toxic, physiologically acceptable). In other embodiments, the salts include those useful in, for example, though not limited to, the preparation, isolation or purification of (S)—N-(3,4-difluoro-2-(2-fluoro-4-iodophenylamino)-6-methoxyphenyl)-1-(2,3-dihydroxypropyl)cyclopropane-1-sulfonamide.

(S)—N-(3,4-difluoro-2-(2-fluoro-4-iodophenylamino)-6-methoxyphenyl)-1-(2,3-dihydroxypropyl)cyclopropane-1-sulfonamide may form salts with alkali metals such as sodium, potassium and lithium, with alkaline earth metals such as calcium and magnesium, with organic bases such as dicyclohexylamine, tributylamine, pyridine and amino acids such as arginine, lysine and the like. Such salts can be formed as known to those skilled in the art.

(S)—N-(3,4-difluoro-2-(2-fluoro-4-iodophenylamino)-6-methoxyphenyl)-1-(2,3-dihydroxypropyl)cyclopropane-1-sulfonamide with a variety of organic and inorganic acids. Such salts include those formed with hydrogen chloride, hydrogen bromide, methanesulfonic acid, sulfuric acid, acetic acid, trifluoroacetic acid, oxalic acid, maleic acid, benzenesulfonic acid, toluenesulfonic acid and various others (e.g., nitrates, phosphates, borates, tartrates, citrates, succinates, benzoates, ascorbates, salicylates and the like). Such salts can be formed as known to those skilled in the art.

Stereoisomers (S)—N-(3,4-difluoro-2-(2-fluoro-4-iodophenylamino)-6-methoxyphenyl)-1-(2,3-dihydroxypropyl)cyclopropane-1-sulfonamide occurs as the (S) stereoisomer. The present invention also encompasses the use of the (R)-isomer in the compositions and methods described herein, as well as mixtures of the (S) and the (R) isomers. Thus, both stereoisomers are contemplated, either in admixture or in pure or substantially pure form. The racemic forms can be resolved by physical methods, such as, for example, fractional crystallization, separation or crystallization of diastereomeric derivatives or separation by chiral column chromatography. The individual optical isomers can be obtained from the racemates from the conventional methods, such as, for example, salt formation with an optically active acid followed by crystallization.

Isobolograms

The interaction that occurs between two drugs can be described as (A) synergistic, (B) additive (zero interaction) or (C) antagonistic. In a synergistic interaction, the effect of a combination is greater than expected from the individual dose-response curves (also described as super-additivity), thus there is "positive interaction" between the drugs when administered in combination. In some instances, it is possible to determine from experimental measurements whether or not different drugs interact to produce a particular effect. One such method is the isobolographic method which is based on the use of equieffective doses/concentrations of individual drugs and the combinations thereof. Dose-response relations can be used to construct a model giving the expected effect of a combination.

If $d_a$ and $d_b$ are doses of drugs A and B given in combination, and $D_a$ and $D_b$ are the doses of drugs A and B that when given separately produce an isoeffective response with the combination. Isoboles (iso-effect curves) can be constructed based on the assumption that there is no interaction between the drugs when used in combination. The combination ($d_a$, $d_b$) is represented by a point on a graph which has axes representing doses of the individual drugs. If the drugs do not interact, and their relative effects are simply additive, this point will fall on a straight line (isobole) connecting the two axes between the values representing doses ($D_a$ and $D_b$) isoeffective with the combination ($d_a$, $d_b$). The equation for the zero interaction isobole for two compounds is:

$$\frac{d_a}{D_a} + \frac{d_b}{D_b} = 1$$

Effects are additive; zero interaction $da$ = dose of $A$; $db$ = dose of $B$ – given in combination $Da$ = dose of $A$; $Db$ = dose of $B$ – given separately If the effect of the combination is greater than expected from the individual dose-response curves the interaction is synergistic, with smaller amounts of $d_a$ and/or $d_b$ needed to produce an equipotent effect to $D_a$ and $D_b$ (both unchanged), thus:

$$\frac{d_a}{D_a} + \frac{d_b}{D_b} < 1$$

Effects are synergistic

If the effect of the combination is less than expected from the individual dose-response curves, it can be considered an antagonistic interaction and greater amounts of $d_a$ and/or $d_b$ are needed to produce an equipotent effect to $D_a$ and $D_b$:

$$\frac{d_a}{D_a} + \frac{d_b}{D_b} > 1$$

Effects are antagonistic

FIG. 1 presents graphical representations of the curves for zero interaction (additive effects only), antagonistic and synergistic interactions. Put simply, any graph showing points below the straight, series 1 line can be considered to be synergistic drug combinations.

Methods of Use

In some embodiments, a compound and/or composition disclosed herein is administered to treat a proliferative disorder in an individual in need thereof. In some embodiments, the proliferative disorder is an abnormal cell growth. In some embodiments, the proliferative disorder is a hemangioma. In some embodiments, the proliferative disorder is a cancer. In some embodiments, the cancer is a hematologic cancer and/or nonhematologic cancer. In some embodiments, the cancer is multiple myeloma, a leukemia, and/or a lymphoma. In some embodiments, the cancer is an acute leukemia, and/or a chronic leukemia. In some embodiments, the cancer is acute lymphocytic leukemia (ALL) and/or acute nonlymphocytic leukemia (ANLL). In some embodiments, the cancer is chronic lymphocytic leukemia (CLL) and/or chronic myelogenous leukemia (CML). In some embodiments, the cancer is Hodgkin's lymphoma and/or non-Hodgkin's lymphoma. In some embodiments, the cancer is multiple myeloma. In some embodiments, the cancer is of low, intermediate, or high grade. In some embodiments, the cancer is: brain cancer, a cancer of the head and/or neck, lung cancer, breast cancer, a cancer of the reproductive system, a cancer of the digestive system, pancreatic cancer, and/or a cancer of the urinary system. In some embodiments, the cancer is a cancer of the upper digestive tract or colorectal cancer. In some embodiments, the cancer is bladder cancer or renal cell carcinoma. In some embodiments, the cancer is prostate cancer. In some embodiments, the cancer is breast cancer (e.g., a ductal carcinoma in duct tissue in a mammary gland, medullary carcinomas, colloid carcinomas, tubular carcinomas, and/or inflammatory breast cancer; ovarian cancer, including epithelial ovarian tumors (e.g., adenocarcinoma in the ovary and/or an adenocarcinoma that has migrated from the ovary into the abdominal cavity; uterine cancer; cervical cancer (e.g., (e.g., adenocarcinoma in the cervix epithelial including squamous cell carcinoma and/or adenocarcinoma); prostate cancer (e.g., (e.g., prostate cancer selected from the following: an adenocarcinoma or an adenocarinoma that has migrated to the bone); pancreatic cancer (e.g., epitheliod carcinoma in the pancreatic duct tissue and/or an adenocarcinoma in a pancreatic duct); bladder cancer (e.g., (e.g., a transitional cell carcinoma in urinary bladder, urothelial carcinomas (transitional cell carcinomas), tumors in the urothelial cells that line the bladder, squamous cell carcinomas, adenocarcinomas, and/or small cell cancers); leukemia (e.g., acute myeloid leukemia (AML), acute lymphocytic leukemia, chronic lymphocytic leukemia, chronic myeloid leukemia, hairy cell leukemia, myelodysplasia, and/or a myeloproliferative disorder); bone cancer; lung cancer (e.g., non-small cell lung cancer (NSCLC), which is divided into squamous cell carcinomas, adenocarcinomas, and/or large cell undifferentiated carcinomas, and/or small cell lung cancer); skin cancer (e.g., basal cell carcinoma, melanoma, squamous cell carcinoma and/or actinic keratosis); eye retinoblastoma; cutaneous or intraocular (eye) melanoma; primary liver cancer (cancer that begins in the liver); kidney cancer; thyroid cancer (e.g., papillary, follicular, medullary and/or anaplastic); AIDS-related lymphoma (e.g., diffuse large B-cell lymphoma, B-cell immunoblastic lymphoma and/or small non-cleaved cell lymphoma); Kaposi's Sarcoma; viral-induced cancers (e.g., hepatitis B virus (HBV), hepatitis C virus (HCV), and/or hepatocellular carcinoma); human lymphotropic virus-type 1 (HTLV-1) and/or adult T-cell leukemia/lymphoma; human papilloma virus (HPV) cervical cancer; a central nervous system cancer (CNS) (e.g., primary brain tumor, which includes gliomas (astrocytoma, anaplastic astrocytoma, or glioblastoma multiforme), Oligodendroglioma, Ependymoma, Meningioma, Lymphoma, Schwannoma, and/or Medulloblastoma); a peripheral nervous system (PNS) cancer (e.g., acoustic neuromas and/or malignant peripheral nerve sheath tumor (MPNST) including neurofibromas and/or schwannomas, malignant fibrous cytoma, malignant fibrous histiocytoma, malignant meningioma, malignant mesothelioma, and/or malignant mixed Müllerian tumor); an oral cavity or oropharyngeal cancer (e.g., hypopharyngeal cancer, laryngeal cancer, nasopharyngeal cancer, and/or oropharyngeal cancer); stomach cancer (e.g., lymphomas, gastric stromal tumors, and/or carcinoid tumors); testicular cancer (e.g., germ cell tumors (GCTs), which include seminomas and/or nonseminomas, and/or gonadal stromal tumors, which include Leydig cell tumors and/or Sertoli cell tumors); thymus cancer (e.g., thymomas, thymic carcinomas, Hodgkin disorder, non-Hodgkin lymphomas carcinoids or carcinoid tumors); rectal cancer; colon cancer, renal cancer, adrenocortical carcinoma, follicular lymphoma, pre-B acute leukemia, chronic lymphocytic B-leukemia, adenocarcinoma, angiosarcoma, astrocytoma, acoustic neuroma, anaplastic astrocytoma, basal cell carcinoma, blastoglioma, chondrosarcoma, choriocarcinoma, chordoma, craniopharyngioma, cutaneous melanoma, cystadenocarcinoma, endotheliosarcoma, embryonal carcinoma, ependymoma, Ewing's tumor, epithelial carcinoma, fibrosarcoma, gastric cancer, genitourinary tract cancers, glioblastoma multiforme, hemangioblastoma, hepatocellular carcinoma, hepatoma, Kaposi's sarcoma, large cell carcinoma, leiomyosarcoma, liposarcoma, lymphangiosarcoma, lymphangioendotheliosarcoma, medullary thyroid carcinoma, medulloblastoma, meningioma mesothelioma, myelomas, myxosarcoma neuroblastoma, neurofibrosarcoma, oligodendroglioma, osteogenic sarcoma, epithelial ovarian cancer, papillary carcinoma, papillary adenocarcinomas, parathyroid tumors, pheochromocytoma, pinealoma, plasmacytomas, retinoblastoma, rhabdomyosarcoma, sebaceous gland carcinoma, seminoma, skin cancers, melanoma, small cell lung carcinoma, squamous cell carcinoma, sweat gland carcinoma, synovioma, thyroid cancer, uveal melanoma, Wilm's tumor, a cancer of oral cavity and/or pharynx, a cancer of the respiratory system, a cancers of a bone and/or joint, a cancer of soft tissue, a skin cancer, a cancer of the genital system, a cancers of the eye and/or orbit, a cancers of the nervous system, a cancer of the lymphatic system, and/or a cancer of the endocrine system. In certain embodiments, these cancer is cancer of the tongue, mouth, pharynx, or other oral cavity; esophageal cancer, stomach cancer, or cancer of the small intestine; colon cancer or rectal, anal, or anorectal cancer; cancer of the liver, intrahepatic bile duct, gallbladder, pancreas, or other biliary or digestive organs; laryngeal, bronchial, or other cancers of the respiratory organs; heart cancer, melanoma, basal cell carcinoma, squamous cell carcinoma, other non-epithelial skin cancer; uterine or cervical cancer; uterine corpus cancer; ovarian, vulvar, vaginal, or other female genital cancer; prostate, testicular, penile or other male genital cancer; urinary bladder cancer; cancer of the kidney; renal, pelvic, or urethral cancer or other cancer of the genito-urinary organs; thyroid cancer or other endocrine cancer; chronic lymphocytic leukemia; and/orcutaneous T-cell lymphoma, both granulocytic monocytic.

In certain instances, inhibition of the Raf-MEK-ERK signaling pathway, elicits pancreatic cancer cell In some embodiments, a compound and/or composition disclosed herein is administered to degrade, inhibit the growth of or to kill a cell. In some embodiments, the cell is a cancer cell. In some embodiments, the cell is a brain, breast, lung, ovarian, pancreatic, prostate, renal, or colorectal cancer cell.

In some embodiments, a compound and/or composition disclosed herein is administered to inhibit the growth of a target cell. In some embodiments, the growth of a target cell is about 1% inhibited relative to the growth rate preceding administration of a compound and/or composition disclosed herein. In some embodiments, the growth of a target cell is about 2% inhibited relative to the growth rate preceding administration of a compound and/or composition disclosed herein. In some embodiments, the growth of a target cell is about 3% inhibited relative to the growth rate preceding administration of a compound and/or composition disclosed herein. In some embodiments, the growth of a target cell is about 4% inhibited relative to the growth rate preceding administration of a compound and/or composition disclosed herein. In some embodiments, the growth of a target cell is about 5% inhibited relative to the growth rate preceding administration of a compound and/or composition disclosed herein. In some embodiments, the growth of a target cell is about 10% inhibited relative to the growth rate preceding administration of a compound and/or composition disclosed herein. In some embodiments, the growth of a target cell is about 20% inhibited relative to the growth rate preceding administration of a compound and/or composition disclosed herein. In some embodiments, the growth of a target cell is about 25% inhibited relative to the growth rate preceding administration of a compound and/or composition disclosed herein. In some embodiments, the growth of a target cell is about 30% inhibited relative to the growth rate preceding administration of a compound and/or composition disclosed herein. In some embodiments, the growth of a target cell is about 40% inhibited relative to the growth rate preceding administration of a compound and/or composition disclosed herein. In some embodiments, the growth of a target cell is about 50% inhibited relative to the growth rate preceding administration of a compound and/or composition disclosed herein. In some embodiments, the growth of a target cell is about 60% inhibited relative to the growth rate preceding administration of a compound and/or composition disclosed herein. In some embodiments, the growth of a target cell is about 70% inhibited relative to the growth rate preceding administration of a compound and/or composition disclosed herein. In some embodiments, the growth of a target cell is about 75% inhibited relative to the growth rate preceding administration of a compound and/or composition disclosed herein. In some embodiments, the growth of a target cell is about 80% inhibited relative to the growth rate preceding administration of a compound and/or composition disclosed herein. In some embodiments, the growth of a target cell is about 90% inhibited relative to the growth rate preceding administration of a compound and/or composition disclosed herein. In some embodiments, the growth of a target cell is about 100% inhibited relative to the growth rate preceding administration of a compound and/or composition disclosed herein. In some embodiments, the target cell is a cancer cell.

In some embodiments, a compound and/or composition disclosed herein is administered to degrade a target cell. In some embodiments, a compound and/or composition disclosed herein is administered to degrade a plurality of target cells. In some embodiments, 1% of the target cells are degraded. In some embodiments, 2% of the target cells are degraded. In some embodiments, 3% of the target cells are degraded. In some embodiments, 4% of the target cells are degraded. In some embodiments, 5% of the target cells are degraded. In some embodiments, 10% of the target cells are degraded. In some embodiments, 20% of the target cells are degraded. In some embodiments, 25% of the target cells are degraded. In some embodiments, 30% of the target cells are degraded. In some embodiments, 40% of the target cells are degraded. In some embodiments, 50% of the target cells are degraded. In some embodiments, 60% of the target cells are degraded. In some embodiments, 70% of the target cells are degraded. In some embodiments, 75% of the target cells are degraded. In some embodiments, 80% of the target cells are degraded. In some embodiments, 90% of the target cells are degraded. In some embodiments, 100% of the target cells are degraded. In some embodiments, essentially all of the target cells are degraded. In some embodiments, the target cells are cancer cells.

In some embodiments, a compound and/or composition disclosed herein is administered to kill a target cell. In some embodiments, a compound and/or composition disclosed herein is administered to kill a plurality of target cells. In some embodiments, 1% of the target cells are killed. In some embodiments, 2% of the target cells are killed. In some embodiments, 3% of the target cells are killed. In some embodiments, 4% of the target cells are killed. In some embodiments, 5% of the target cells are killed. In some embodiments, 10% of the target cells are killed. In some embodiments, 20% of the target cells are killed. In some embodiments, 25% of the target cells are killed. In some embodiments, 30% of the target cells are killed. In some embodiments, 40% of the target cells are killed. In some embodiments, 50% of the target cells are killed. In some embodiments, 60% of the target cells are killed. In some embodiments, 70% of the target cells are killed. In some embodiments, 75% of the target cells are killed. In some embodiments, 80% of the target cells are killed. In some embodiments, 90% of the target cells are killed. In some embodiments, 100% of the target cells are killed. In some embodiments, the target cells are cancer cells.

In some embodiments, a compound and/or composition disclosed herein is administered to reduce the size of a tumor, inhibit tumor growth, reduce metastasis or prevent metastasis in an individual in need thereof.

In some embodiments, the size of a tumor is reduced. In some embodiments, the size of a tumor is reduced by at least 1%. In some embodiments, the size of a tumor is reduced by at least 2%. In some embodiments, the size of a tumor is reduced by at least 3%. In some embodiments, the size of a tumor is reduced by at least 4%. In some embodiments, the size of a tumor is reduced by at least 5%. In some embodiments, the size of a tumor is reduced by at least 10%. In some embodiments, the size of a tumor is reduced by at least 20%. In some embodiments, the size of a tumor is reduced by at least 25%. In some embodiments, the size of a tumor is reduced by at least 30%. In some embodiments, the size of a tumor is reduced by at least 40%. In some embodiments, the size of a tumor is reduced by at least 50%. In some embodiments, the size of a tumor is reduced by at least 60%. In some embodiments, the size of a tumor is reduced by at least 70%. In some embodiments, the size of a tumor is reduced by at least 75%. In some embodiments, the size of a tumor is reduced by at least 80%. In some embodiments, the size of a tumor is reduced by at least 85%. In some embodiments, the size of a tumor is reduced by at least 90%. In some embodiments, the size of a tumor is reduced by at least 95%.

In some embodiments, tumor growth is inhibited. In some embodiments, tumor growth is inhibited by at least 1% relative to the growth rate preceding administration of a compound and/or composition disclosed herein. In some embodiments, tumor growth is inhibited by at least 2% relative to the growth rate preceding administration of a compound and/or composition disclosed herein. In some embodiments, tumor growth is inhibited by at least 3% relative to the growth rate preceding administration of a compound and/or composition disclosed herein. In some embodiments, tumor growth is inhibited by at least 4% relative to the growth rate preceding administration of a compound and/or composition disclosed herein. In some embodiments, tumor growth is inhibited by at least 5% relative to the growth rate preceding administration of a compound and/or composition disclosed herein. In some embodiments, tumor growth is inhibited by at least 6% relative to the growth rate preceding administration of a compound and/or composition disclosed herein. In some embodiments, tumor growth is inhibited by at least 10% relative to the growth rate preceding administration of a compound and/or composition disclosed herein. In some embodiments, tumor growth is inhibited by at least 20% relative to the growth rate preceding administration of a compound and/or composition disclosed herein. In some embodiments, tumor growth is inhibited by at least 30% relative to the growth rate preceding administration of a compound and/or composition disclosed herein. In some embodiments, tumor growth is inhibited by at least 40% relative to the growth rate preceding administration of a compound and/or composition disclosed herein. In some embodiments, tumor growth is inhibited by at least 50% relative to the growth rate preceding administration of a compound and/or composition disclosed herein. In some embodiments, tumor growth is inhibited by at least 60% relative to the growth rate preceding administration of a compound and/or composition disclosed herein. In some embodiments, tumor growth is inhibited by at least 70% relative to the growth rate preceding administration of a compound and/or composition disclosed herein. In some embodiments, tumor growth is inhibited by at least 75% relative to the growth rate preceding administration of a compound and/or composition disclosed herein. In some embodiments, tumor growth is inhibited by at least 80% relative to the growth rate preceding administration of a compound and/or composition disclosed herein. In some embodiments, tumor growth is inhibited by at least 90% relative to the growth rate preceding administration of a compound and/or composition disclosed herein. In some embodiments, tumor growth is inhibited by at least 95% relative to the growth rate preceding administration of a compound and/or composition disclosed herein. In some embodiments, tumor growth is inhibited by at least 99% relative to the growth rate preceding administration of a compound and/or composition disclosed herein.

In some embodiments, metastasis is inhibited. In some embodiments, metastasis is inhibited by at least 1% relative to the growth rate preceding administration of a compound and/or composition disclosed herein. In some embodiments, metastasis is inhibited by at least 2% relative to the growth rate preceding administration of a compound and/or composition disclosed herein. In some embodiments, metastasis is inhibited by at least 3% relative to the growth rate preceding administration of a compound and/or composition disclosed herein. In some embodiments, metastasis is inhibited by at least 4% relative to the growth rate preceding administration of a compound and/or composition disclosed herein. In some embodiments, metastasis is inhibited by at least 5% relative to the growth rate preceding administration of a compound and/or composition disclosed herein. In some embodiments, metastasis is inhibited by at least 6% relative to the growth rate preceding administration of a compound and/or composition disclosed herein. In some embodiments, metastasis is inhibited by at least 10% relative to the growth rate preceding administration of a compound and/or composition disclosed herein. In some embodiments, metastasis is inhibited by at least 20% relative to the growth rate preceding administration of a compound and/or composition disclosed herein. In some embodiments, metastasis is inhibited by at least 30% relative to the growth rate preceding administration of a compound and/or composition disclosed herein. In some embodiments, metastasis is inhibited by at least 40% relative to the growth rate preceding administration of a compound and/or composition disclosed herein. In some embodiments, metastasis is inhibited by at least 50% relative to the growth rate preceding administration of a compound and/or composition disclosed herein. In some embodiments, metastasis is inhibited by at least 60% relative to the growth rate preceding administration of a compound and/or composition disclosed herein. In some embodiments, metastasis is inhibited by at least 70% relative to the growth rate preceding administration of a compound and/or composition disclosed herein. In some embodiments, metastasis is inhibited by at least 75% relative to the growth rate preceding administration of a compound and/or composition disclosed herein. In some embodiments, metastasis is inhibited by at least 80% relative to the growth rate preceding administration of a compound and/or composition disclosed herein. In some embodiments, metastasis is inhibited by at least 90% relative to the growth rate preceding administration of a compound and/or composition disclosed herein. In some embodiments, metastasis is inhibited by at least 95% relative to the growth rate preceding administration of a compound and/or composition disclosed herein. In some embodiments, metastasis is inhibited by at least 99% relative to the growth rate preceding administration of a compound and/or composition disclosed herein. In some embodiments, metastasis is prevented.

MEK

In certain instances, a proliferative disorder of a plurality of cells is partially or fully caused by oncogenic Ras signaling and its effect on cyclin kinase inhibitors such as $p27^{kip1}$.

In certain instances, Ras is a signal transduction protein. In certain instances, Ras is activated by the binding of guanosine nucleotides, GTP (Guanosine triphosphate) or GDP (Guanosine diphosphate).

In certain instances, the activation of Ras results in the activation of a cascade of serine/threonine kinases. In certain instances, activated Ras activates Raf proteins. In certain instances, activated Raf proteins activate "MEK1" and "MEK2."

MEK1 and MEK2 are dual-function serine/threonine and tyrosine protein kinases that, in certain instances, activate MAPK. In certain instances, activation of MAP kinase by mitogens appears induces cellular proliferation. In certain instances, constitutive activation of MAPK induces cellular transformation. In certain instances, blockade of downstream Ras signaling, as by use of a dominant negative Raf-1 protein, inhibits mitogenesis, whether induced from cell surface receptors or from oncogenic Ras mutants.

Pharmaceutical Compositions

Disclosed herein, in certain embodiments, is a pharmaceutical composition comprising (a) a therapeutically-effective amount of (S)—N-(3,4-difluoro-2-(2-fluoro-4-iodophenylamino)-6-methoxyphenyl)-1-(2,3-dihydroxypropyl)cyclopropane-1-sulfonamide, a salt thereof, or a polymorph thereof (see e.g., U.S. application Ser. No. 12/399,848); and (b) a second active agent selected from an agent that treats cancer. In some embodiments, the second active agent is selected from an agent disclosed in Table 1.

In some embodiments, the pharmaceutical composition further comprises at least one pharmaceutically acceptable carrier. In some embodiments, the pharmaceutical composition further comprises an adjuvant, excipient, preservative, agent for delaying absorption, filler, binder, adsorbent, buffer, disintegrating agent, and/or solubilizing agent.

In some embodiments, the pharmaceutical composition further comprises at least one pharmaceutically acceptable carrier. Suitable pharmaceutical carriers include inert diluents or fillers, water and/or various organic solvents.

In some embodiments, the composition includes a filler or diluent. In various embodiments, the filler or diluent is microcrystalline cellulose, silicified microcrystalline cellulose, lactose, mannitol, compressible sugar, calcium phosphate, calcium sulfate, calcium carbonate, calcium silicate and/or starch. In other embodiments, the filler or diluent is microcrystalline cellulose.

In some embodiments, the composition includes a disintegrant. In various embodiments, the disintegrant is croscarmellose sodium, sodium starch glycolate, crospovidone, methylcellulose, alginic acid, sodium alginate, starch derivatives, betonite and/or veegum. In some embodiment, the disintegrant is croscarmellose sodium.

In some embodiments, the composition includes a lubricant. In various embodiments, the lubricant is magnesium stearate, metallic stearates, talc, sodium stearyl fumarate and/or stearic acid. In some embodiments, the lubricant is magnesium stearate.

In some embodiments, the composition includes a wetting agent or surfactant. In various embodiments, the wetting agent or surfactant is sodium lauryl sulfate, glycerol, sorbitan oleates, sorbitan stearates, polyoxyethylenated sorbitan laurate, palmitate, stearate, oleate or hexaolate, polyoxyethylene stearyl alcohol and/or sorbitan monolaurate. In some embodiments, the wetting agent or surfactant is sodium lauryl sulfate.

Additional excipients (e.g., glidants, flavors, and/or colorants) can also be added. For additional excipients see The Handbook of Pharmaceutical Excipients, $5^{th}$ Edition, 2005 and/or the FDA Inactive Ingredient database.

In some embodiments, the composition comprises microcrystalline cellulose. In some embodiments, the composition comprises croscarmellose sodium. In some embodiments, the composition comprises sodium lauryl sulfate. In some embodiments, the composition comprises magnesium stearate.

In some embodiments, the composition further comprises a filler selected from microcrystalline cellulose, silicified microcrystalline cellulose, lactose, a compressible sugar, xylitol, sorbitol, mannitol, pregelatinized starch, maltodextrin, calcium phosphate, calcium carbonate, starch and/or a calcium silicate. In some embodiments, the composition further comprises a disintegrant selected from croscarmellose sodium, sodium starch glycolate, crospovidone, methylcellulose, alginic acid, sodium alginate, starch derivatives, betonite and/or veegum. In some embodiments, the composition further comprises a lubricant selected from magnesium stearate, metallic stearates, talc, sodium stearyl fumarate and/or stearic acid. In some embodiments, the composition further comprises a wetting agent or surfactant selected from sodium lauryl sulfate, glycerol, sorbitan oleates, sorbitan stearates, polyoxyethylenated sorbitan laurate, palmitate, stearate, oleate or hexaolate, polyoxyethylene stearyl alcohol and/or sorbitan monolaurate.

Dosage Forms

In some embodiments, a composition disclosed herein is formulated for oral administration. In some embodiments, a composition disclosed herein is administered as a tablet, capsule, pill, powder, solution, suspension, a gel cap, a caplet, a pellet, or a bead.

In some embodiments, a compositing disclosed herein is administered via a tablet. In some embodiments, a tablet comprises an inert diluent (e.g., calcium carbonate, sodium carbonate, lactose, calcium phosphate or sodium phosphate); a granulating and/or disintegrating agent (e.g., croscarmellose sodium, crospovidone or sodium starch glycolate); a filler (e.g., microcrystalline cellulose, silicified microcrystalline cellulose, pregelatinized starch, lactose, dicalcium phosphate, or compressible sugar); a binder (e.g., hypromellose, povidone, starch, gelatin, polyvinyl-pyrrolidone, or acacia); a surfactant (e.g., sodium lauryl sulfate) and/or a lubricant and/or processing aide (e.g., talc, sodium croscarmellose, corn starch, or alginic acid, magnesium stearate, stearic acid, colloidal silicon dioxide, and/or sodium lauryl sulfate). In some embodiments, a tablet further comprises a sweetening agent, a flavoring agent, a coloring agent and/or a preserving agent.

In some embodiments, a tablet comprises citric acid, a disintegrant (e.g., starch, alginic acid and/or certain complex silicates), and/or a binding agent (e.g., sucrose, gelatin and/or acacia).

In some embodiments, the tablet is un-coated or coated. In certain instances, a coating masks the taste of a composition. In certain instances, a coating modifies disintegration and/or absorption in the gastrointestinal tract.

In some embodiments, a tablet disclosed herein is prepared according to any suitable method. In some embodiments, a tablet disclosed herein is prepared by dry blending. In some embodiments, a compound disclosed herein is incorporated into the dosage form by dry blending with an excipient followed by compression into a tablet form. In some embodiments, a compressed tablet is prepared by compressing in a suitable machine the active ingredient in a free-flowing form (e.g., a powder or granules), optionally mixed with a binder, an inert diluent, and/or a lubricating, surface active or dispersing agent.

In some embodiments, a tablet disclosed herein is prepared according to any suitable method. In some embodiments, a tablet disclosed herein is prepared by wet granulation. In some embodiments, a compound disclosed herein is added to the dry excipients and mixed prior to the addition of the binder solution, or the drug substance is dissolved and added as a solution as part of granulation. In the wet granulation technique the surfactant, if used, is added to the dry excipients or added to the binder solution and incorporated in a solution form.

In some embodiments, a compositing disclosed herein is administered via a capsule. In some embodiments, the capsule is a hard capsule. In some embodiments, the active ingredient is mixed with an inert solid diluent, for example, calcium carbonate, calcium phosphate or kaolin. In some embodiments, the capsule is a soft capsule. In some embodiments, the active ingredient is mixed with water soluble carrier such as polyethyleneglycol or an oil medium, for example peanut oil, liquid paraffin, or olive oil.

In some embodiments, a capsule disclosed herein is prepared according to any suitable method. In some embodiments, a compound disclosed herein is dissolved in a material (e.g., a molten form of a high molecular weight polyethylene glycol) that is filled into a hard gelatin capsule shell that is subsequently banded and sealed. In some embodiments, a compound disclosed herein is dissolved a molten form of a high molecular weight polyethylene glycol. In some embodiments, the mixture is cooled and then filled into a gelatin capsule.

In some embodiments, the composition is in the form of a capsule or tablet and/or has a total weight of about 50 mg to about 1000 mg. In some embodiments, the composition is in the form of a capsule or tablet and/or has a total weight selected from the group consisting of 50 mg, 75 mg, 100 mg, 150 mg, 200 mg, 250 mg, 300 mg, 350 mg, 400 mg, 450 mg, and/or 500 mg. In some embodiments, the composition is in the form of a capsule or tablet and/or has a total weight of about 240 mg.

In some embodiments, the composition is in the form of a capsule or tablet and the dosage form comprises from about 1 to about 50 mg of a compound disclosed herein, having a USP acceptance value for content uniformity of less than about 15.

In some embodiments, a compound disclosed herein is administered as an aqueous suspension. In some embodiments, an aqueous suspension comprises a sweetening or flavoring agent, coloring matters or dyes and, if desired, emulsifying agents or suspending agents, together with diluents water, ethanol, propylene glycol, glycerin, or combinations thereof. In some embodiments, an aqueous suspension comprises a suspending agent. In some embodiments, an aqueous suspension comprises sodium carboxymethylcellulose, methylcellulose, hydroxypropylmethyl-cellulose, sodium alginate, polyvinyl-pyrrolidone, gum tragacanth and/or gum acacia. In some embodiments, an aqueous suspension comprises a dispersing or wetting agent. In some embodiments, an aqueous suspension comprises a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethylene-oxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. In some embodiments, an aqueous suspension comprises a preservative. In some embodiments, an aqueous suspension comprises ethyl, or n-propyl p-hydroxybenzoate. In some embodiments, an aqueous suspension comprises a sweetening agent. In some embodiments, an aqueous suspension comprises sucrose, saccharin or aspartame.

In some embodiments, a compound disclosed herein is administered as an oily suspension. In some embodiments, an oily suspension is formulated by suspending the active ingredient in a vegetable oil (e.g., arachis oil, olive oil, sesame oil or coconut oil), or in mineral oil (e.g., liquid paraffin). In some embodiments, an oily suspension comprises a thickening agent (e.g., beeswax, hard paraffin or cetyl alcohol). In some embodiments, an oily suspension comprises sweetening agents (e.g., those set forth above). In some embodiments, an oily suspension comprises an anti-oxidant (e.g., butylated hydroxyanisol or alpha-tocopherol).

In some embodiments, a composition disclosed herein is formulated for parenteral injection (e.g., via injection or infusion, including intraarterial, intracardiac, intradermal, intraduodenal, intramedullary, intramuscular, intraosseous, intraperitoneal, intrathecal, intravascular, intravenous, intravitreal, epidural and/or subcutaneous). In some embodiments, a composition disclosed herein is administered as a sterile solution, suspension or emulsion.

In some embodiments, a formulation for parenteral administration includes aqueous and/or non-aqueous (oily) sterile injection solutions of the active compounds which may contain antioxidants, buffers, bacteriostats and/or solutes which render the formulation isotonic with the blood of the intended recipient; and/or aqueous and/or non-aqueous sterile suspensions which may include a suspending agent and/or a thickening agent. In some embodiments, a formulation for parenteral administration includes suitable stabilizers or agents which increase the solubility of the compounds to allow for the preparation of highly concentrated solutions.

In some embodiments, a compound disclosed herein is administered as an aqueous suspension. In some embodiments, an aqueous suspension comprises water, Ringer's solution and/or isotonic sodium chloride solution.

In some embodiments, a compound disclosed herein is administered as an oil-in-water microemulsion where the active ingredient is dissolved in the oily phase. In some embodiments, a compound disclosed herein is dissolved in a fatty oil (e.g., sesame oil, or synthetic fatty acid esters, (e.g., ethyl oleate or triglycerides, or liposomes. In some embodiments, a compound disclosed herein is dissolved in a mixture of soybean oil andrlecithin. In some embodiments, the oil solution is introduced into a water and glycerol mixture and processed to form a microemulsion.

In some embodiments, a composition formulated for parenteral administration is administered as a single bolus shot. In some embodiments, a composition formulated for parenteral administration is administered via a continuous intravenous delivery device (e.g., Deltec CADD-PLUS™ model 5400 intravenous pump).

In some embodiments, a formulation for injection is presented in unit dosage form, e.g., in ampoules or in multi-dose containers, with an added preservative. In some embodiments, a formulation for injection is stored in powder form or in a freeze-dried (lyophilized) condition requiring only the addition of the sterile liquid carrier, for example, saline or sterile pyrogen-free water, immediately prior to use.

In some embodiments, a formulation disclosed herein is administered by depot preparation. In some embodiments, a depot preparation is administered by implantation (for example subcutaneously or intramuscularly) or by intramuscular injection.

In some embodiments, a composition disclosed herein is formulated for topical administration. As used herein, topical administration means application of a composition such that the compound does not significantly enter the blood stream. In some embodiments, a composition disclosed herein is applied to the epidermis, the buccal cavity, the ear, eye and/or nose.

In some embodiments, a composition formulated for topical administration is formulated as a gel, liniment, lotion, cream, ointment or paste, solution, suspension, emulsion, or powder. In some embodiments, a composition disclosed herein is administered as an ointment or cream. In some embodiments, a composition disclosed herein is administered as a mouth wash. In some embodiments, a composition disclosed herein is administered via inhalation.

In some embodiments, a composition formulated for administration via inhalation is delivered from an insufflator, nebulizer pressurized packs or other convenient means of delivering an aerosol spray. Pressurized packs may comprise a suitable propellant such as dichlorodifluoromethane, trichlorofluoromethane, dichlorotetrafluoroethane, carbon dioxide or other suitable gas. In the case of a pressurized aerosol, the dosage unit is determined by providing a valve to deliver a metered amount. Alternatively, for administration by inhalation or insufflation, pharmaceutical preparations may take the form of a dry powder composition, for example a powder mix of the compound and a suitable powder base such as lactose or starch. The powder composition is presented in unit dosage form, in for example, capsules, cartridges, gelatin or blister packs from which the powder is administered with the aid of an inhalator or insufflator. For buccal or sublingual administration, the compositions may take the form of tablets, lozenges, pastilles, or gels formulated in conventional manner. Such compositions may comprise the active ingredient in a flavored basis such as sucrose and acacia or tragacanth.

In some embodiments, a composition disclosed herein is formulated for rectal administration. In some embodiments, a composition disclosed herein is administered as a suppository. In some embodiments, a composition suitable for rectal administration is prepared by mixing a compound disclosed herein with a suitable non-irritating excipient which is solid at ordinary temperatures but liquid at the rectal temperature and will therefore melt in the rectum to release the drug. In some embodiments, a composition suitable for rectal administration is prepared by mixing a compound disclosed herein with cocoa butter, glycerinated gelatin, hydrogenated vegetable oils, mixtures of polyethylene glycols of various molecular weights or fatty acid esters of polyethylene glycol.

For methods of preparing various pharmaceutical compositions see Remington's Pharmaceutical Sciences, Mack Publishing Company, Ester, Pa., 18th Edition (1990).

In some embodiments, the dosage form releases at least 60 percent of the drug within 30 minutes using U.S. Pharmacopeia (USP) Apparatus II at 50 rpm with 1% sodium lauryl sulfate in water as the dissolution medium. In some embodiments, the dosage form releases about 60-100 percent of the drug within 30 minutes using U.S. Pharmacopeia (USP) Apparatus II at 50 rpm with 1% sodium lauryl sulfate in water as the dissolution medium. In some embodiments, the dosage form releases about 60-90 percent of the drug within 30 minutes using U.S. Pharmacopeia (USP) Apparatus II at 50 rpm with 1% sodium lauryl sulfate in water as the dissolution medium. In some embodiments, the dosage form releases about 60-80 percent of the drug within 30 minutes using U.S. Pharmacopeia (USP) Apparatus II at 50 rpm with 1% sodium lauryl sulfate in water as the dissolution medium.

Dosages

The amount of pharmaceutical compositions administered will firstly be dependent on the mammal being treated. In the instances where pharmaceutical compositions are administered to a human subject, the daily dosage will normally be determined by the prescribing physician with the dosage generally varying according to the age, sex, diet, weight, general health and response of the individual individual, the severity of the individual's symptoms, the precise indication or condition being treated, the severity of the indication or condition being treated, time of administration, route of administration, the disposition of the composition, rate of excretion, drug combination, and the discretion of the prescribing physician.

In some embodiments, the dosage is between about 0.001 to about 1000 mg/kg body weight/day. In some embodiments, the amount of compound disclosed herein is in the range of about 0.5 to about 50 mg/kg/day. In some embodiments, the amount of compound disclosed herein is is about 0.001 to about 7 g/day. In some embodiments, the amount of compound disclosed herein is about 0.01 to about 7 g/day. In some embodiments, the amount of compound disclosed herein is about 0.02 to about 5 g/day. In some embodiments, the amount of compound disclosed herein is about 0.05 to about 2.5 g/day. In some embodiments, the amount of compound disclosed herein is about 0.1 to about 1 g/day.

In some embodiments, the amount of compound disclosed herein is administered in a single dose, once daily. In some embodiments, the amount of compound disclosed herein is administered in multiple doses, more than once per day. In some embodiments, the amount of compound disclosed herein is administered twice daily. In some embodiments, the amount of compound disclosed herein is administered three times per day. In some embodiments, the amount of compound disclosed herein is administered four times per day. In some embodiments, the amount of compound disclosed herein is administered more than four times per day.

In some instances, dosage levels below the lower limit of the aforesaid range is more than adequate, while in other cases still larger doses is employed without causing any harmful side effect, e.g. by dividing such larger doses into several small doses for administration throughout the day. The amount administered will vary depending on the particular $IC_{50}$ value of the compound used. In combinational applications in which the compound is not the sole therapy, it is possible to administer lesser amounts of compound and still have therapeutic or prophylactic effect.

EXAMPLES

Example 1

Isobolograms—General Protocol

Source of Materials:

The following materials were obtained from the sources indicated. 96 well cell culture plates (Becton-Dickinson, North Ryde, NSW, Australia). CellTiter-Blue® (Alamar Blue™) Cell Viability Assay (Promega, Madison, Wis. USA). DMEM, MEM, and RPMI 1640 cell culture media, FBS, HBSS, sodium pyruvate, Glutamax, and penicillinstreptomycin (Invitrogen Australia, Mt Waverley, VIC, Australia). Trypan Blue (Sigma-Aldrich, Castle Hill, NSW, Australia). Saline (Baxter Australia, NSW, Australia). Spectramax Gemini XPS Fluorometer (Adelab Scientific, Adelaide, SA, Australia). The human lung carcinoma cell line A549, the human renal adenocarcinoma cell lines ACHN and 786-O, the human colorectal adenocarcinoma cell line Colo205, the human breast cancer cell lines MCF-7 and MDA-MB231, the human myeloma cell line RPMI-8226, the human glioblastoma cell line U87G, the human pancreatic cancer cell line MiaPaCa-2, the thyroid cancer cell line SW579, and the human melanoma cell line G361 were sourced from the American Type Culture Collection (ATCC) (Rockville, Md., USA).

Cell Production:

A549 cells, ACHN cells, Colo205 cells, G361 cells, MCF-7 cells, RPMI-8226 cells and 786-O cells were cultured in RPMI 1640 cell culture medium, supplemented with 10% FBS, 100 IU/mL penicillinstreptomycin, 1 mM sodium pyruvate, and 2 mM Glutamax. MDA-MB231 cells, MiaPaCa-2 cells and SW579 cells (from ATCC master stock) were cultured in DMEM cell culture medium, supplemented with 10% FBS, 100 IU/mL penicillin-streptomycin, 1 mM sodium pyruvate, and 2 mM Glutamax. U87G cells were cultured in MEM cell culture medium, supplemented with 10% FBS, 100 IU/mL penicillin-streptomycin, 1 mM sodium pyruvate, and 2 mM Glutamax.

All cells were grown at 37° C. in humidified cell culture incubators supplied with 95% air/5% $CO_2$. All adherent cells were used at a maximum passage number of 10, with the exception of MiaPaCa-2 cells for the combination with Imatinib, which was used at passage 11.

Cell Seeding:

Cell stock suspensions were diluted in the appropriate culture medium. 50 µL of these dilutions were added 96 well plates, to give seeding concentrations of 5000 cells/well for all cell lines, except for RPMI-8226 cells which were seeded at 25000 cells/well.

Combination Assay:

For combination assays, two 96 well plates were seeded for each cell line and Test Article combination. Test Articles were added to cells 24 hours post-seeding.

Initial Test Article concentrations were chosen based on the calculated $IC_{50}$ for the particular cell line, such that the $IC_{50}$ fell around the mid concentration of the dilution series. 48 hours post-addition of Test Articles, the CellTiter-Blue® Assay was carried out on all plates.

CellTiter-Blue® Assay:

Following incubation, 10 uL of CellTiter-Blue® was added to each well and incubated for up to 4 hours. Fluorescence was then measured using a Spectramax Gemini XPS Fluorometer. All data were recorded and entered into Microsoft Excel spreadsheets for interpretation.

Calculations:

Data collected from CellTiter-Blue® assays were plotted as dose response curves for $IC_{50}$ determination, and as isobolograms to assess synergism or antagonism of Test Article combinations. For $IC_{50}$ determination, growth inhibition was calculated and plotted against compound concentration. In these plots, the X-axis (compound concentration) was represented in a logarithmic scale. $IC_{50}$ concentration was calculated as the half maximal (50%) inhibitory concentration (IC) for each compound.

Test Articles (TA):

The test articles used are as follows, with abbreviations indicated (for ease of identification):

| Chemical name | Chemical structure | Abbreviated to: |
|---|---|---|
| (S)-N-(3,4-difluoro-2-(2-fluoro-4-iodophenylamino)-6-methoxyphenyl)-1-(2,3-dihydroxypropyl)cyclopropane-1-sulfonamide | 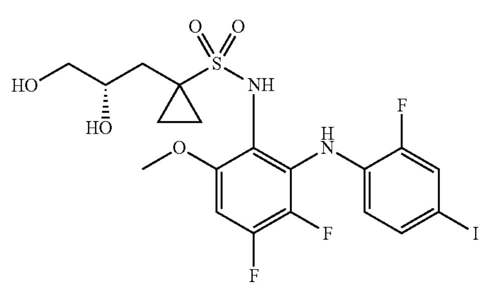 [SMILES: COc1cc(F)c(F)c(Nc2ccc(I)cc2F)c1NS(=O)(=O)C1(C[C@H](O)CO)CC1] | TA1 |

-continued

| Chemical name | Chemical structure | Abbreviated to: |
|---|---|---|
| 3-(6,7-bis(2-methoxyethoxy)quinazolin-4-ylamino)benzonitrile | 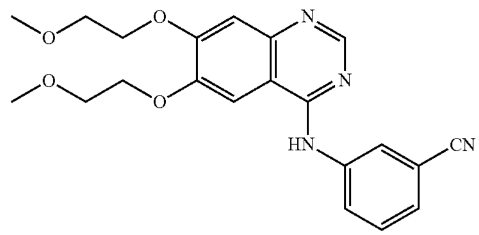 [SMILES: COCCOc1cc2ncnc(Nc3cccc(C#N)c3)c2cc1OCCOC] | TA2 |
| N-(3-chloro-4-fluorophenyl)-7-methoxy-6-(3-morpholinopropoxy)quinazolin-4-amine | 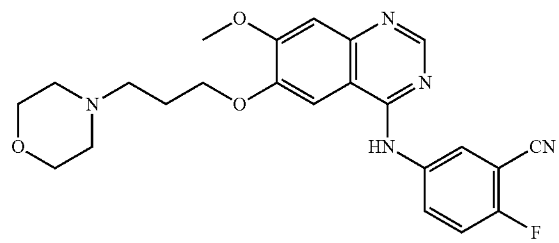 [SMILES: COc1cc2ncnc(Nc3ccc(F)c(C#N)c3)c2cc1OCCCN1CCOCC1] | TA3 |
| 4-amino-1-[3,3-difluoro-4-hydroxy-5-(hydroxymethyl) tetrahydrofuran-2-yl]-1H-pyrimidin-2-one | 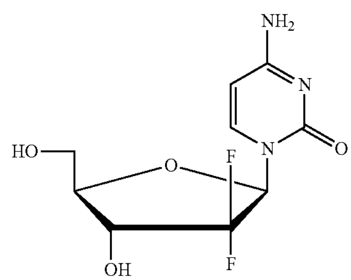 | TA4 |
| N-hydroxy-N'-phenyl-octanediamide | 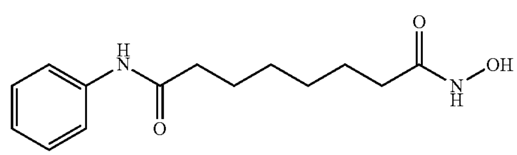 [SMILES: O=C(CCCCCCC(=O)Nc1ccccc1)NO] | TA5 |
| 4-methyl-5-oxo-2,3,4,6,8-pentazabicyclo[4.3.0] nona-2,7,9-triene-9-carboxamide | 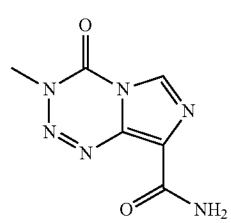 | TA6 |
| N-[3-chloro-4-[(3-fluorophenyl)methoxy]phenyl]-6-[5-[(2-methylsulfonylethylamino)methyl]-2-furyl]quinazolin-4-amine | 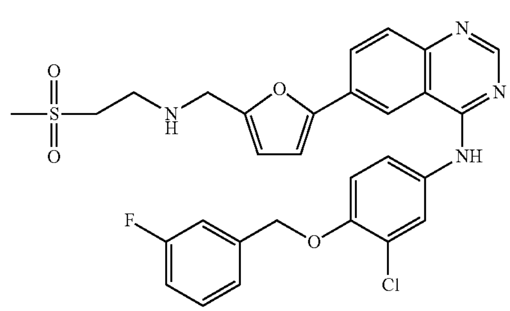 [SMILES: CS(=O)(=O)CCNCc1ccc(-c2ccc3ncnc(Nc4ccc(OCc5cccc(F)c5)c(Cl)c4)c3c2)o1] | TA7 |

-continued

| Chemical name | Chemical structure | Abbreviated to: |
|---|---|---|
| (1R,2R,4S)-4-{(2R)-2-[(3S,6R,7E,9R,10R,12R,14S,15E,17E,19E,21S,23S,26R,27R,34aS)-9,27-dihydroxy-10,21-dimethoxy-6,8,12,14,20,26-hexamethyl-1,5,11,28,29-pentaoxo-1,4,5,6,9,10,11,12,13,14,21,22,23,24,25,26,27,28,29,31,32,33,34,34a-tetracosahydro-3H-23,27-epoxypyrido[2,1-c][1,4]oxazacyclohentriacontin-3-yl]propyl}-2-methoxycyclohexyl 3-hydroxy-2-(hydroxymethyl)-2-methylpropanoate | (structure) | TA8 |
| Dihydroxy-12-[(2R)-1-[(1S,3R,4R)-4-(2-hydroxyethoxy)-3-methoxycyclohexyl]propan-2-yl]-19,30-dimethoxy-15,17,21,23,29,35-hexamethyl-11,36-dioxa-4-azatricyclo[30.3.1.0 4,9]hexatriaconta-16,24,26,28-tetraene-2,3,10,14,20-pentone | (structure) | TA9 |

Examples 2-29

According to the protocol described above, the following combinations of compounds were assayed for synergistic activity, in the cell lines indicated. The resulting graphs are shown in the figures indicated. In instances where the assay was run in duplicate, both graphs are presented. If the combinations showed synergy, the graphs are presented; if no synergy was observed at the concentrations assayed, in the particular cell line, no figure/graph is presented.

| Eg | 1st TA | 2nd TA | Tumor Type | Cell line | Fig |
|---|---|---|---|---|---|
| 2 | TA1 | TA2 | NSCLC | A549 | 2 |
| 3 | TA1 | TA3 | NSCLC | A549 | 3 |
| 4 | TA1 | TA3 | Breast Cancer | MDA-MB231 | 4 |
| 5 | TA1 | TA3 | Thyroid Cancer | SW579 | 5 |
| 6 | TA1 | TA4 | NSCLC | A549 | 6 |
| 7 | TA1 | TA4 | Melanoma | G361 | 7 |
| 8 | TA1 | TA4 | Breast Cancer | MCF-7 | 8 |
| 9 | TA1 | TA4 | Pancreatic | MiaPaCa-2 | 9 |
| 10 | TA1 | TA4 | Thyroid Cancer | SW579 | 10 |
| 11 | TA1 | TA5 | Thyroid Cancer | SW579 | 11 |
| 12 | TA1 | TA6 | Melanoma | G361 | 12 |
| 13 | TA1 | TA7 | Breast Cancer | MCF-7 | 13 |
| 14 | TA1 | TA7 | Thyroid Cancer | SW579 | 14 |
| *15 | TA1 | TA8 | Adenocarcinoma | AGS | 15 |
| *16 | TA1 | TA8 | Hepatoma | Hep3B | 16 |
| *17 | TA1 | TA9 | Colon Cancer | HCT-116 | 17 |
| 18 | TA1 | TA2 | Melanoma | A375 | — |
| 19 | TA1 | TA3 | Melanoma | A375 | — |
| 20 | TA1 | TA3 | Hepatoma | Hep3B | — |
| 21 | TA1 | TA4 | Breast Cancer | MDA-MB231 | — |
| 22 | TA1 | TA4 | Hepatoma | Hep3B | — |
| 23 | TA1 | TA5 | NSCLC | A549 | — |
| 24 | TA1 | TA5 | Hepatoma | Hep3B | — |
| 25 | TA1 | TA5 | Myeloma | RPMI8226 | — |

| Eg | 1st TA | 2nd TA | Tumor Type | Cell line | Fig |
|---|---|---|---|---|---|
| 26 | TA1 | TA6 | Glioma | U87G | — |
| 27 | TA1 | TA7 | Hepatoma | Hep3B | — |
| *28 | TA1 | TA8 | Renal Carcinoma | ACHN | |
| *29 | TA1 | TA9 | Stomach Cancer | Hs746 | |

*Examples 15, 16, 17, 28, 29: Calculations and graphs in slightly different format Cell lines were obtained from the American Type Culture Collection ((ATCC) (Rockville, Md., USA) and routinely cultured as recommended in DMEM/F12 media+10% fetal bovine serum (FBS) (AGS stomach cancer cells), EMEM medium+10% FBS (Hep3B hepatoma cells), McCoy's medium+10% FBS (HCT-116 colon cancer cells).

Figure 15:
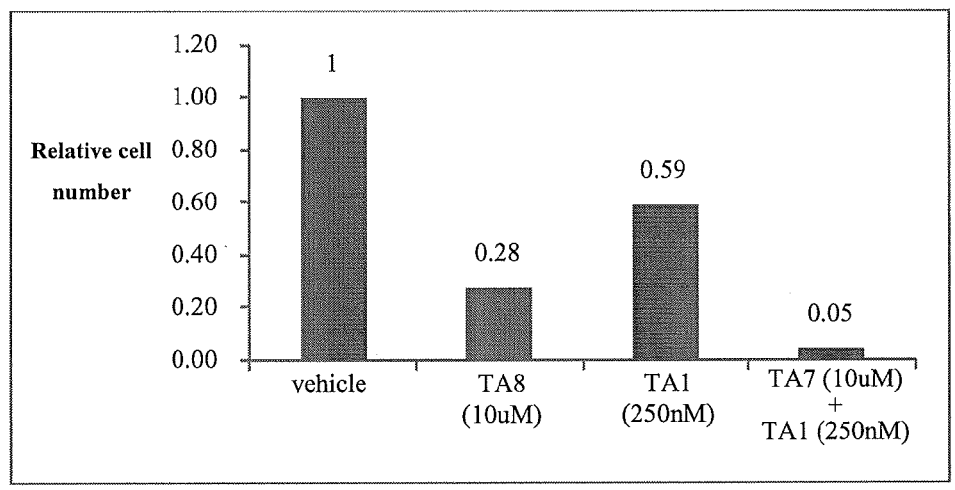
FIG. 15 shows relative cell numbers after 3 day treatment with TA1 and/or TA8 in human adenocarcinoma AGS cells (two different doses).
Figure 15:
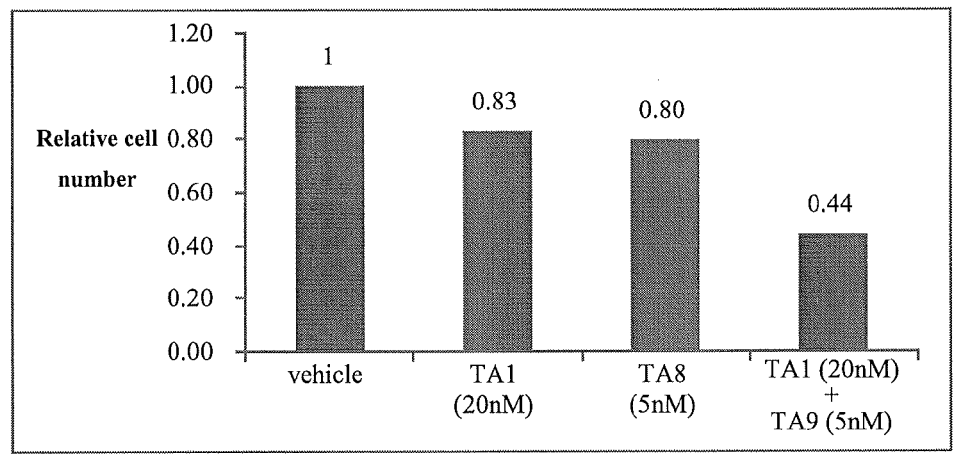
Figure 16:
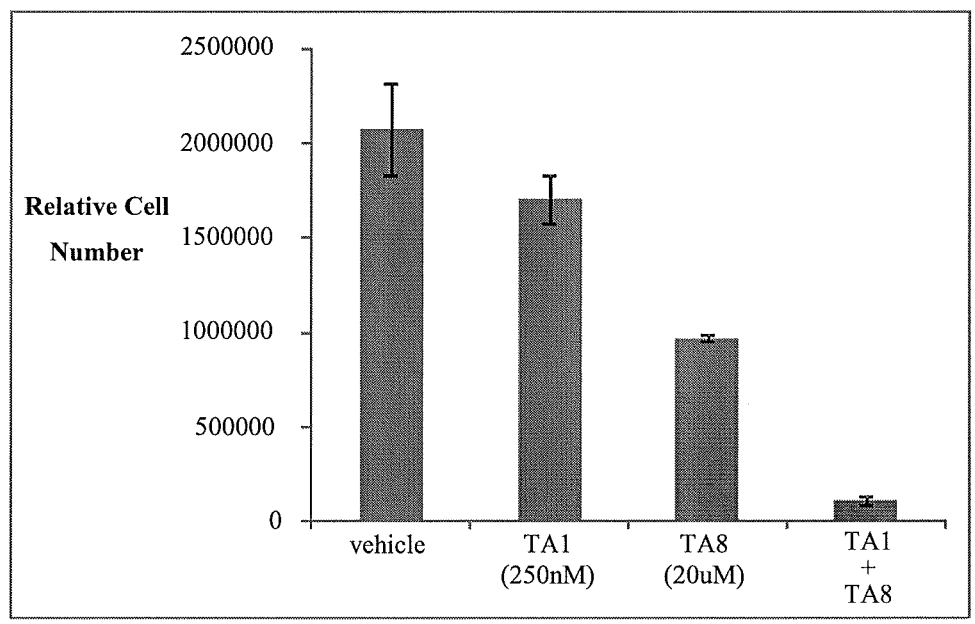
FIG. 16 shows relative cell numbers after 4 day treatment with TA1 and/or TA8 in hepatoma Hep3B cells.
Figure 17:
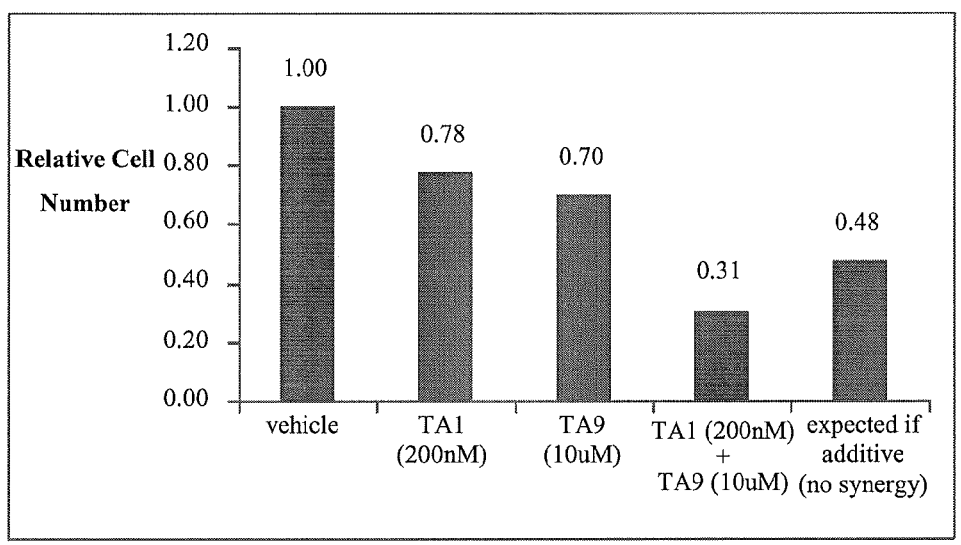
FIG. 17 shows relative cell numbers after treatment with TA1 and/or TA9 in HCT-116 colon cancer cells.

Cells were plated in 96-well clear bottom, white sided, tissue culture plates at a density of 1,000 to 5,000 cells per well (depending on the cell type). The following day, cells were treated with vehicle only, or combinations of TA1 and the indicated second test article (TA8 or TA9) at the dose indicated. Following 3-6 days of treatment, the relative viable cell number was quantitated using The Cell Titer-Glo Luminescent Cell Viability Assay (Promega Corp, Madison, Wis.) according to the manufacturers' instructions. All experiments were carried out in triplicate in the 96-well plate, and results shown are typical of multiple experiments. The graphs in FIGS. 15, 16, 17 show mean values.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A method of treating or preventing non-small cell lung cancer, breast cancer, thyroid cancer, melanoma, or pancreatic cancer, comprising administering to an individual in need thereof a synergistic combination of
    a. a therapeutically-effective amount of (S)—N-(3,4-difluoro-2-(2-fluoro-4-iodophenylamino)-6-methoxyphenyl)-1-(2,3-dihydroxypropyl) cyclopropane-1-sulfonamide, a salt thereof, or a polymorph thereof; and
    b. a therapeutically-effective amount of 4-amino-1-[3,3-difluoro-4-hydroxy-5-(hydroxymethyl) tetrahydrofuran-2-yl]-1H-pyrimidin-2-one:

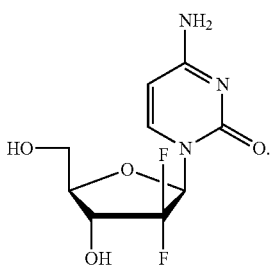 [SMILES: Nc1ccn([C@@H]2O[C@H](CO)[C@H](O)C2(F)F)c(=O)n1]

2. A method according to claim 1, which is for treating non-small cell lung cancer, breast cancer, thyroid cancer, melanoma, or pancreatic cancer.

3. A method according to claim 1, further comprising administering an additional therapy, wherein the additional therapy is radiation therapy.

4. A method according to claim 1, further comprising administering an additional therapy, wherein the additional therapy comprises administering one or more additional chemotherapeutic agents.

5. A composition, comprising:
    a. a therapeutically-effective amount of (S)—N-(3,4-difluoro-2-(2-fluoro-4-iodophenylamino)-6-methoxyphenyl)-1-(2,3-dihydroxypropyl)cyclopropane-1-sulfonamide, a salt thereof, or a polymorph thereof; and
    b. a therapeutically-effective amount of 4-amino-1-[3,3-difluoro-4-hydroxy-5-(hydroxymethyl)tetrahydrofuran-2-yl]-1H-pyrimidin-2-one:

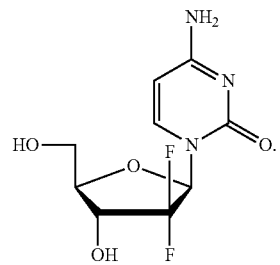 [SMILES: Nc1ccn([C@@H]2O[C@H](CO)[C@H](O)C2(F)F)c(=O)n1]

6. A composition according to claim 5, further comprising a pharmaceutically acceptable carrier.

7. A composition according to claim 5, further comprising one or more additional chemotherapeutic agents.

8. A kit for treating a subject having cancer, comprising:
    i) a composition according to claim 5; and
    ii) instructions for administration of the composition to treat cancer.

9. A method of treating or preventing non-small cell lung cancer, breast cancer, thyroid cancer, melanoma, pancreatic cancer, adenocarcinoma, hepatoma, or colon cancer, comprising administering to a subject in need thereof an effective amount of a composition according to claim 5.

10. A method according to claim 9, which is for treating non-small cell lung cancer.

11. A method according to claim 9, which is for treating breast cancer.

12. A method according to claim 9, which is for treating thyroid cancer.

13. A method according to claim 9, which is for treating melanoma.

14. A method according to claim 9, which is for treating pancreatic cancer.

15. A method according to claim 9, which is for treating adenocarcinoma.

16. A method according to claim 9, which is for treating hepatoma.

17. A method according to claim 9, which is for treating colon cancer.

* * * * *